(12) United States Patent
Hoarau et al.

(10) Patent No.: US 8,352,009 B2
(45) Date of Patent: *Jan. 8, 2013

(54) MEDICAL SENSOR AND TECHNIQUE FOR USING THE SAME

(75) Inventors: Carine Hoarau, Lafayette, CA (US); Li Li, Petaluma, CA (US)

(73) Assignee: Covidien LP, Mansfield, MA (US)

( * ) Notice: Subject to any disclaimer, the term of this patent is extended or adjusted under 35 U.S.C. 154(b) by 1027 days.

This patent is subject to a terminal disclaimer.

(21) Appl. No.: 12/348,742

(22) Filed: Jan. 5, 2009

(65) Prior Publication Data

US 2009/0118598 A1 May 7, 2009

Related U.S. Application Data

(63) Continuation of application No. 11/240,682, filed on Sep. 30, 2005, now Pat. No. 7,483,731.

(51) Int. Cl.
*A61B 5/1455* (2006.01)
(52) U.S. Cl. ...................................... 600/344; 600/310
(58) Field of Classification Search .................. 600/310, 600/322, 323, 335, 344
See application file for complete search history.

(56) References Cited

U.S. PATENT DOCUMENTS

| | | |
|---|---|---|
| 3,403,555 A | 10/1968 | Versaci et al. |
| 3,536,545 A | 10/1970 | Traynor et al. |
| D222,454 S | 10/1971 | Beeber |
| 3,721,813 A | 3/1973 | Condon et al. |
| 4,098,772 A | 7/1978 | Bonk et al. |
| D250,275 S | 11/1978 | Bond |
| D251,387 S | 3/1979 | Ramsay et al. |
| D262,488 S | 12/1981 | Rossman et al. |
| 4,334,544 A | 6/1982 | Hill et al. |
| 4,350,165 A | 9/1982 | Striese |
| 4,353,372 A | 10/1982 | Ayer |
| 4,380,240 A | 4/1983 | Jobsis et al. |
| 4,406,289 A | 9/1983 | Wesseling et al. |
| 4,510,551 A | 4/1985 | Brainard, II |
| 4,586,513 A | 5/1986 | Hamaguri |
| 4,603,700 A | 8/1986 | Nichols et al. |
| 4,621,643 A | 11/1986 | New, Jr. et al. |
| 4,653,498 A | 3/1987 | New, Jr. et al. |
| 4,677,528 A | 6/1987 | Miniet |
| 4,685,464 A | 8/1987 | Goldberger et al. |
| 4,694,833 A | 9/1987 | Hamaguri |
| 4,697,593 A | 10/1987 | Evans et al. |

(Continued)

FOREIGN PATENT DOCUMENTS

DE 3405444 8/1985

(Continued)

OTHER PUBLICATIONS

Rheineck-Leyssius, Aart t., et al.; "Advanced Pulse Oximeter Signal Processing Technology Compared to Simple Averaging: I. Effect on Frequency of Alarms in the Operating Room," *Journal of clinical Anestesia*, vol. 11, pp. 192-195 (1990).

(Continued)

*Primary Examiner* — Eric Winakur
(74) *Attorney, Agent, or Firm* — Fletcher Yoder

(57) ABSTRACT

A sensor may be adapted to provide output to indicate when the sensor experiences abnormal forces or pressure. The forces may be outside forces, or the forces may be generated by patient motion. A sensor system as provided may also be adapted to correct for such forces when calculating measurements related to a physiological characteristic.

20 Claims, 7 Drawing Sheets

U.S. PATENT DOCUMENTS

| | | | |
|---|---|---|---|
| 4,700,708 A | 10/1987 | New, Jr. et al. |
| 4,714,080 A | 12/1987 | Edgar, Jr. et al. |
| 4,714,341 A | 12/1987 | Hamaguri et al. |
| 4,722,120 A | 2/1988 | Lu |
| 4,726,382 A | 2/1988 | Boehmer et al. |
| 4,759,369 A | 7/1988 | Taylor |
| 4,770,179 A | 9/1988 | New, Jr. et al. |
| 4,773,422 A | 9/1988 | Isaacson et al. |
| 4,776,339 A | 10/1988 | Schreiber |
| 4,781,195 A | 11/1988 | Martin |
| 4,783,815 A | 11/1988 | Buttner |
| 4,796,636 A | 1/1989 | Branstetter et al. |
| 4,800,495 A | 1/1989 | Smith |
| 4,800,885 A | 1/1989 | Johnson |
| 4,802,486 A | 2/1989 | Goodman et al. |
| 4,805,623 A | 2/1989 | Jöbsis |
| 4,807,630 A | 2/1989 | Malinouskas |
| 4,807,631 A | 2/1989 | Hersh et al. |
| 4,819,646 A | 4/1989 | Cheung et al. |
| 4,819,752 A | 4/1989 | Zelin |
| 4,824,242 A | 4/1989 | Frick et al. |
| 4,825,872 A | 5/1989 | Tan et al. |
| 4,825,879 A | 5/1989 | Tan et al. |
| 4,830,014 A | 5/1989 | Goodman et al. |
| 4,832,484 A | 5/1989 | Aoyagi et al. |
| 4,846,183 A | 7/1989 | Martin |
| 4,848,901 A | 7/1989 | Hood, Jr. |
| 4,854,699 A | 8/1989 | Edgar, Jr. |
| 4,859,056 A | 8/1989 | Prosser et al. |
| 4,859,057 A | 8/1989 | Taylor et al. |
| 4,863,265 A | 9/1989 | Flower et al. |
| 4,865,038 A | 9/1989 | Rich et al. |
| 4,867,557 A | 9/1989 | Takatani et al. |
| 4,869,253 A | 9/1989 | Craig, Jr. et al. |
| 4,869,254 A | 9/1989 | Stone et al. |
| 4,880,304 A | 11/1989 | Jaeb et al. |
| 4,883,055 A | 11/1989 | Merrick |
| 4,883,353 A | 11/1989 | Hansmann et al. |
| 4,890,619 A | 1/1990 | Hatschek |
| 4,892,101 A | 1/1990 | Cheung et al. |
| 4,901,238 A | 2/1990 | Suzuki et al. |
| 4,908,762 A | 3/1990 | Suzuki et al. |
| 4,911,167 A | 3/1990 | Corenman et al. |
| 4,913,150 A | 4/1990 | Cheung et al. |
| 4,926,867 A | 5/1990 | Kanda et al. |
| 4,927,264 A | 5/1990 | Shiga et al. |
| 4,928,692 A | 5/1990 | Goodman et al. |
| 4,934,372 A | 6/1990 | Corenman et al. |
| 4,938,218 A | 7/1990 | Goodman et al. |
| 4,942,877 A | 7/1990 | Sakai et al. |
| 4,948,248 A | 8/1990 | Lehman |
| 4,955,379 A | 9/1990 | Hall |
| 4,960,126 A | 10/1990 | Conlon et al. |
| 4,964,408 A | 10/1990 | Hink et al. |
| 4,971,062 A | 11/1990 | Hasebe et al. |
| 4,974,591 A | 12/1990 | Awazu et al. |
| 5,007,423 A | 4/1991 | Branstetter et al. |
| 5,025,791 A | 6/1991 | Niwa |
| RE33,643 E | 7/1991 | Isaacson et al. |
| 5,028,787 A | 7/1991 | Rosenthal et al. |
| 5,035,243 A | 7/1991 | Muz |
| 5,040,539 A | 8/1991 | Schmitt et al. |
| 5,041,187 A | 8/1991 | Hink et al. |
| 5,054,488 A | 10/1991 | Muz |
| 5,055,671 A | 10/1991 | Jones |
| 5,058,588 A | 10/1991 | Kaestle |
| 5,065,749 A | 11/1991 | Hasebe et al. |
| 5,066,859 A | 11/1991 | Karkar et al. |
| 5,069,213 A | 12/1991 | Polczynski |
| 5,078,136 A | 1/1992 | Stone et al. |
| 5,084,327 A | 1/1992 | Stengel |
| 5,086,229 A | 2/1992 | Rosenthal et al. |
| 5,088,493 A | 2/1992 | Giannini et al. |
| 5,090,410 A | 2/1992 | Saper et al. |
| 5,094,239 A | 3/1992 | Jaeb et al. |
| 5,094,240 A | 3/1992 | Muz |
| 5,099,841 A | 3/1992 | Heinonen et al. |
| 5,099,842 A | 3/1992 | Mannheimer et al. |
| H1039 H | 4/1992 | Tripp, Jr. et al. |
| 5,104,623 A | 4/1992 | Miller |
| 5,109,849 A | 5/1992 | Goodman et al. |
| 5,111,817 A | 5/1992 | Clark et al. |
| 5,113,861 A | 5/1992 | Rother |
| D326,715 S | 6/1992 | Schmidt |
| 5,125,403 A | 6/1992 | Culp |
| 5,127,406 A | 7/1992 | Yamaguchi |
| 5,131,391 A | 7/1992 | Sakai et al. |
| 5,140,989 A | 8/1992 | Lewis et al. |
| 5,152,296 A | 10/1992 | Simons |
| 5,154,175 A | 10/1992 | Gunther |
| 5,158,082 A | 10/1992 | Jones |
| 5,170,786 A | 12/1992 | Thomas et al. |
| 5,188,108 A | 2/1993 | Secker et al. |
| 5,190,038 A | 3/1993 | Polson et al. |
| 5,193,542 A | 3/1993 | Missanelli et al. |
| 5,193,543 A | 3/1993 | Yelderman |
| 5,203,329 A | 4/1993 | Takatani et al. |
| 5,209,230 A | 5/1993 | Swedlow et al. |
| 5,213,099 A | 5/1993 | Tripp et al. |
| 5,216,598 A | 6/1993 | Branstetter et al. |
| 5,217,012 A | 6/1993 | Young et al. |
| 5,217,013 A | 6/1993 | Lewis et al. |
| 5,218,207 A | 6/1993 | Rosenthal |
| 5,218,962 A | 6/1993 | Mannheimer et al. |
| 5,224,478 A | 7/1993 | Sakai et al. |
| 5,226,417 A | 7/1993 | Swedlow et al. |
| 5,228,440 A | 7/1993 | Chung et al. |
| 5,237,994 A | 8/1993 | Goldberger |
| 5,239,185 A | 8/1993 | Ito et al. |
| 5,246,002 A | 9/1993 | Prosser |
| 5,246,003 A | 9/1993 | DeLonzor |
| 5,247,931 A | 9/1993 | Norwood |
| 5,247,932 A | 9/1993 | Chung et al. |
| 5,249,576 A | 10/1993 | Goldberger et al. |
| 5,253,645 A | 10/1993 | Friedman et al. |
| 5,253,646 A | 10/1993 | Delpy et al. |
| 5,259,381 A | 11/1993 | Cheung et al. |
| 5,259,761 A | 11/1993 | Schnettler et al. |
| 5,263,244 A | 11/1993 | Centa et al. |
| 5,267,562 A | 12/1993 | Ukawa et al. |
| 5,267,563 A | 12/1993 | Swedlow et al. |
| 5,267,566 A | 12/1993 | Choucair et al. |
| 5,273,036 A | 12/1993 | Kronberg et al. |
| 5,275,159 A | 1/1994 | Griebel |
| 5,278,627 A | 1/1994 | Aoyagi et al. |
| 5,279,295 A | 1/1994 | Martens et al. |
| 5,285,783 A | 2/1994 | Secker |
| 5,285,784 A | 2/1994 | Seeker |
| 5,287,853 A | 2/1994 | Vester et al. |
| 5,291,884 A | 3/1994 | Heinemann et al. |
| 5,297,548 A | 3/1994 | Pologe |
| 5,299,120 A | 3/1994 | Kaestle |
| 5,299,570 A | 4/1994 | Hatschek |
| 5,309,908 A | 5/1994 | Freidman et al. |
| 5,311,865 A | 5/1994 | Mayeux |
| 5,313,940 A | 5/1994 | Fuse et al. |
| 5,323,776 A | 6/1994 | Blakeley et al. |
| 5,329,922 A | 7/1994 | Atlee, III |
| 5,337,744 A | 8/1994 | Branigan |
| 5,339,810 A | 8/1994 | Ivers et al. |
| 5,343,818 A | 9/1994 | McCarthy et al. |
| 5,343,869 A | 9/1994 | Pross et al. |
| 5,348,003 A | 9/1994 | Caro |
| 5,348,004 A | 9/1994 | Hollub et al. |
| 5,348,005 A | 9/1994 | Merrick et al. |
| 5,349,519 A | 9/1994 | Kaestle |
| 5,349,952 A | 9/1994 | McCarthy et al. |
| 5,349,953 A | 9/1994 | McCarthy et al. |
| 5,351,685 A | 10/1994 | Potratz |
| 5,353,799 A | 10/1994 | Chance |
| 5,355,880 A | 10/1994 | Thomas et al. |
| 5,355,882 A | 10/1994 | Ukawa et al. |
| 5,361,758 A | 11/1994 | Hall et al. |
| 5,365,066 A | 11/1994 | Krueger, Jr. et al. |
| 5,368,025 A | 11/1994 | Young et al. |
| 5,368,026 A | 11/1994 | Swedlow et al. |
| 5,368,224 A | 11/1994 | Richardson et al. |

| Patent | Date | Inventor |
|---|---|---|
| 5,372,136 A | 12/1994 | Steuer et al. |
| 5,377,675 A | 1/1995 | Ruskewicz et al. |
| 5,385,143 A | 1/1995 | Aoyagi |
| 5,387,122 A | 2/1995 | Goldberger et al. |
| 5,390,670 A | 2/1995 | Centa et al. |
| 5,392,777 A | 2/1995 | Swedlow et al. |
| 5,398,680 A | 3/1995 | Polson et al. |
| 5,402,777 A | 4/1995 | Warring et al. |
| 5,402,779 A | 4/1995 | Chen et al. |
| 5,411,023 A | 5/1995 | Morris, Sr. et al. |
| 5,411,024 A | 5/1995 | Thomas et al. |
| 5,413,099 A | 5/1995 | Schmidt et al. |
| 5,413,100 A | 5/1995 | Barthelemy et al. |
| 5,413,101 A | 5/1995 | Sugiura |
| 5,413,102 A | 5/1995 | Schmidt et al. |
| 5,417,207 A | 5/1995 | Young et al. |
| 5,421,329 A | 6/1995 | Casciani et al. |
| 5,425,360 A | 6/1995 | Nelson |
| 5,425,362 A | 6/1995 | Siker et al. |
| 5,427,093 A | 6/1995 | Ogawa et al. |
| 5,429,128 A | 7/1995 | Cadell et al. |
| 5,429,129 A | 7/1995 | Lovejoy et al. |
| 5,431,159 A | 7/1995 | Baker et al. |
| 5,431,170 A | 7/1995 | Mathews |
| 5,437,275 A | 8/1995 | Amundsen et al. |
| 5,438,986 A | 8/1995 | Disch et al. |
| 5,448,991 A | 9/1995 | Polson et al. |
| 5,452,717 A | 9/1995 | Branigan et al. |
| 5,465,714 A | 11/1995 | Scheuing |
| 5,469,845 A | 11/1995 | DeLonzor et al. |
| RE35,122 E | 12/1995 | Corenman et al. |
| 5,482,034 A | 1/1996 | Lewis et al. |
| 5,482,036 A | 1/1996 | Diab et al. |
| 5,483,646 A | 1/1996 | Uchikoga |
| 5,485,847 A | 1/1996 | Baker, Jr. |
| 5,490,505 A | 2/1996 | Diab et al. |
| 5,490,523 A | 2/1996 | Isaacson et al. |
| 5,491,299 A | 2/1996 | Naylor et al. |
| 5,494,032 A | 2/1996 | Robinson et al. |
| 5,494,043 A | 2/1996 | O'Sullivan et al. |
| 5,497,771 A | 3/1996 | Rosenheimer |
| 5,499,627 A | 3/1996 | Steuer et al. |
| 5,503,148 A | 4/1996 | Pologe et al. |
| 5,505,199 A | 4/1996 | Kim |
| 5,507,286 A | 4/1996 | Solenberger |
| 5,511,546 A | 4/1996 | Hon |
| 5,517,988 A | 5/1996 | Gerhard |
| 5,520,177 A | 5/1996 | Ogawa et al. |
| 5,521,851 A | 5/1996 | Wei et al. |
| 5,522,388 A | 6/1996 | Ishikawa et al. |
| 5,524,617 A | 6/1996 | Mannheimer |
| 5,529,064 A | 6/1996 | Rall et al. |
| 5,533,507 A | 7/1996 | Potratz et al. |
| 5,551,423 A | 9/1996 | Sugiura |
| 5,551,424 A | 9/1996 | Morrison et al. |
| 5,553,614 A | 9/1996 | Chance |
| 5,553,615 A | 9/1996 | Carim et al. |
| 5,555,882 A | 9/1996 | Richardson et al. |
| 5,558,096 A | 9/1996 | Palatnik |
| 5,560,355 A | 10/1996 | Merchant et al. |
| 5,564,417 A | 10/1996 | Chance |
| 5,575,284 A | 11/1996 | Athan et al. |
| 5,575,285 A | 11/1996 | Takanashi et al. |
| 5,577,500 A | 11/1996 | Potratz |
| 5,582,169 A | 12/1996 | Oda et al. |
| 5,584,296 A | 12/1996 | Cui et al. |
| 5,588,425 A | 12/1996 | Sackner et al. |
| 5,588,427 A | 12/1996 | Tien |
| 5,590,652 A | 1/1997 | Inai |
| 5,595,176 A | 1/1997 | Yamaura |
| 5,596,986 A | 1/1997 | Goldfarb |
| 5,611,337 A | 3/1997 | Bukta |
| 5,617,852 A | 4/1997 | MacGregor |
| 5,619,992 A | 4/1997 | Guthrie et al. |
| 5,626,140 A | 5/1997 | Feldman et al. |
| 5,629,992 A | 5/1997 | Amersfoort et al. |
| 5,630,413 A | 5/1997 | Thomas et al. |
| 5,632,272 A | 5/1997 | Diab et al. |
| 5,632,273 A | 5/1997 | Suzuki |
| 5,634,459 A | 6/1997 | Gardosi |
| 5,638,593 A | 6/1997 | Gerhardt et al. |
| 5,638,816 A | 6/1997 | Kiani-Azarbayjany et al. |
| 5,638,818 A | 6/1997 | Diab et al. |
| 5,645,060 A | 7/1997 | Yorkey et al. |
| 5,645,440 A | 7/1997 | Tobler et al. |
| 5,660,567 A | 8/1997 | Nierlich et al. |
| 5,662,105 A | 9/1997 | Tien |
| 5,662,106 A | 9/1997 | Swedlow et al. |
| 5,664,270 A | 9/1997 | Bell et al. |
| 5,666,952 A | 9/1997 | Fuse et al. |
| 5,671,529 A | 9/1997 | Nelson |
| 5,673,692 A | 10/1997 | Schulze et al. |
| 5,673,693 A | 10/1997 | Solenberger |
| 5,676,139 A | 10/1997 | Goldberger et al. |
| 5,676,141 A | 10/1997 | Hollub |
| 5,678,544 A | 10/1997 | DeLonzor et al. |
| 5,680,857 A | 10/1997 | Pelikan et al. |
| 5,685,299 A | 11/1997 | Diab et al. |
| 5,685,301 A | 11/1997 | Klomhaus |
| 5,687,719 A | 11/1997 | Sato et al. |
| 5,687,722 A | 11/1997 | Tien et al. |
| 5,692,503 A | 12/1997 | Kuenstner |
| 5,692,505 A | 12/1997 | Fouts |
| 5,709,205 A | 1/1998 | Bukta |
| 5,713,355 A | 2/1998 | Richardson et al. |
| 5,724,967 A | 3/1998 | Venkatachalam |
| 5,727,547 A | 3/1998 | Levinson et al. |
| 5,730,124 A | 3/1998 | Yamauchi |
| 5,731,582 A | 3/1998 | West |
| D393,830 S | 4/1998 | Tobler et al. |
| 5,743,260 A | 4/1998 | Chung et al. |
| 5,743,262 A | 4/1998 | Lepper, Jr. et al. |
| 5,743,263 A | 4/1998 | Baker, Jr. |
| 5,746,206 A | 5/1998 | Mannheimer |
| 5,746,697 A | 5/1998 | Swedlow et al. |
| 5,752,914 A | 5/1998 | Delonzor et al. |
| 5,755,226 A | 5/1998 | Carim et al. |
| 5,758,644 A | 6/1998 | Diab et al. |
| 5,760,910 A | 6/1998 | Lepper, Jr. et al. |
| 5,766,125 A | 6/1998 | Aoyagi et al. |
| 5,766,127 A | 6/1998 | Pologe et al. |
| 5,769,785 A | 6/1998 | Diab et al. |
| 5,772,587 A | 6/1998 | Gratton et al. |
| 5,774,213 A | 6/1998 | Trebino et al. |
| 5,776,058 A | 7/1998 | Levinson et al. |
| 5,776,059 A | 7/1998 | Kaestle |
| 5,779,630 A | 7/1998 | Fein et al. |
| 5,779,631 A | 7/1998 | Chance |
| 5,782,237 A | 7/1998 | Casciani et al. |
| 5,782,756 A | 7/1998 | Mannheimer |
| 5,782,757 A | 7/1998 | Diab et al. |
| 5,782,758 A | 7/1998 | Ausec et al. |
| 5,786,592 A | 7/1998 | Hök |
| 5,788,634 A | 8/1998 | Suda et al. |
| 5,790,729 A | 8/1998 | Pologe et al. |
| 5,792,052 A | 8/1998 | Isaacson et al. |
| 5,795,292 A | 8/1998 | Lewis et al. |
| 5,797,841 A | 8/1998 | DeLonzor et al. |
| 5,800,348 A | 9/1998 | Kaestle |
| 5,800,349 A | 9/1998 | Isaacson et al. |
| 5,803,910 A | 9/1998 | Potratz |
| 5,807,246 A | 9/1998 | Sakaguchi et al. |
| 5,807,247 A | 9/1998 | Merchant et al. |
| 5,807,248 A | 9/1998 | Mills |
| 5,810,723 A | 9/1998 | Aldrich |
| 5,810,724 A | 9/1998 | Gronvall |
| 5,813,980 A | 9/1998 | Levinson et al. |
| 5,817,008 A | 10/1998 | Rafert et al. |
| 5,817,009 A | 10/1998 | Rosenheimer et al. |
| 5,817,010 A | 10/1998 | Hibl |
| 5,818,985 A | 10/1998 | Merchant et al. |
| 5,820,550 A | 10/1998 | Polson et al. |
| 5,823,950 A | 10/1998 | Diab et al. |
| 5,823,952 A | 10/1998 | Levinson et al. |
| 5,827,179 A | 10/1998 | Lichter et al. |
| 5,827,182 A | 10/1998 | Raley et al. |
| 5,829,439 A | 11/1998 | Yokosawa et al. |
| 5,830,135 A | 11/1998 | Bosque et al. |

| Patent No. | Date | Inventor |
|---|---|---|
| 5,830,136 A | 11/1998 | DeLonzor et al. |
| 5,830,137 A | 11/1998 | Scharf |
| 5,839,439 A | 11/1998 | Nierlich et al. |
| RE36,000 E | 12/1998 | Swedlow et al. |
| 5,842,979 A | 12/1998 | Jarman et al. |
| 5,842,981 A | 12/1998 | Larsen et al. |
| 5,842,982 A | 12/1998 | Mannheimer |
| 5,846,190 A | 12/1998 | Woehrle |
| 5,851,178 A | 12/1998 | Aronow |
| 5,851,179 A | 12/1998 | Ritson et al. |
| 5,853,364 A | 12/1998 | Baker, Jr. et al. |
| 5,860,919 A | 1/1999 | Kiani-Azarbayjany et al. |
| 5,865,736 A | 2/1999 | Baker, Jr. et al. |
| 5,871,442 A | 2/1999 | Madarasz et al. |
| 5,879,294 A | 3/1999 | Anderson et al. |
| 5,885,213 A | 3/1999 | Richardson et al. |
| 5,890,929 A | 4/1999 | Mills et al. |
| 5,891,021 A | 4/1999 | Dillon et al. |
| 5,891,022 A | 4/1999 | Pologe |
| 5,891,024 A | 4/1999 | Jarman et al. |
| 5,891,025 A | 4/1999 | Buschmann et al. |
| 5,891,026 A | 4/1999 | Wang et al. |
| 5,902,235 A | 5/1999 | Lewis et al. |
| 5,910,108 A | 6/1999 | Solenberger |
| 5,911,690 A | 6/1999 | Rall |
| 5,912,656 A | 6/1999 | Tham et al. |
| 5,913,819 A | 6/1999 | Taylor et al. |
| 5,916,154 A | 6/1999 | Hobbs et al. |
| 5,916,155 A | 6/1999 | Levinson et al. |
| 5,919,133 A | 7/1999 | Taylor et al. |
| 5,919,134 A | 7/1999 | Diab |
| 5,920,263 A | 7/1999 | Huttenhoff et al. |
| 5,921,921 A | 7/1999 | Potratz et al. |
| 5,922,607 A | 7/1999 | Bernreuter |
| 5,924,979 A | 7/1999 | Swedlow et al. |
| 5,924,980 A | 7/1999 | Coetzee |
| 5,924,982 A | 7/1999 | Chin |
| 5,924,985 A | 7/1999 | Jones |
| 5,934,277 A | 8/1999 | Mortz |
| 5,934,925 A | 8/1999 | Tobler et al. |
| 5,940,182 A | 8/1999 | Lepper, Jr. et al. |
| 5,954,644 A | 9/1999 | Dettling et al. |
| 5,957,840 A | 9/1999 | Terasawa et al. |
| 5,960,610 A | 10/1999 | Levinson et al. |
| 5,961,450 A | 10/1999 | Merchant et al. |
| 5,961,452 A | 10/1999 | Chung et al. |
| 5,964,701 A | 10/1999 | Asada et al. |
| 5,971,930 A | 10/1999 | Elghazzawi |
| 5,978,691 A | 11/1999 | Mills |
| 5,978,693 A | 11/1999 | Hamilton et al. |
| 5,983,120 A | 11/1999 | Groner et al. |
| 5,983,122 A | 11/1999 | Jarman et al. |
| 5,987,343 A | 11/1999 | Kinast |
| 5,991,648 A | 11/1999 | Levin |
| 5,995,855 A | 11/1999 | Kiani et al. |
| 5,995,856 A | 11/1999 | Mannheimer et al. |
| 5,995,858 A | 11/1999 | Kinast |
| 5,995,859 A | 11/1999 | Takahashi |
| 5,997,343 A | 12/1999 | Mills et al. |
| 5,999,834 A | 12/1999 | Wang et al. |
| 6,002,952 A | 12/1999 | Diab et al. |
| 6,005,658 A | 12/1999 | Kaluza et al. |
| 6,006,120 A | 12/1999 | Levin |
| 6,011,985 A | 1/2000 | Athan et al. |
| 6,011,986 A | 1/2000 | Diab et al. |
| 6,014,576 A | 1/2000 | Raley et al. |
| 6,018,673 A | 1/2000 | Chin et al. |
| 6,018,674 A | 1/2000 | Aronow |
| 6,022,321 A | 2/2000 | Amano et al. |
| 6,023,541 A | 2/2000 | Merchant et al. |
| 6,026,312 A | 2/2000 | Shemwell et al. |
| 6,026,314 A | 2/2000 | Amerov et al. |
| 6,031,603 A | 2/2000 | Fine et al. |
| 6,035,223 A | 3/2000 | Baker, Jr. |
| 6,036,642 A | 3/2000 | Diab et al. |
| 6,041,247 A | 3/2000 | Weckstrom et al. |
| 6,044,283 A | 3/2000 | Fein et al. |
| 6,047,201 A | 4/2000 | Jackson, III |
| 6,055,447 A | 4/2000 | Weil |
| 6,061,584 A | 5/2000 | Lovejoy et al. |
| 6,064,898 A | 5/2000 | Aldrich |
| 6,064,899 A | 5/2000 | Fein et al. |
| 6,067,462 A | 5/2000 | Diab et al. |
| 6,073,038 A | 6/2000 | Wang et al. |
| 6,078,829 A | 6/2000 | Uchida |
| 6,078,833 A | 6/2000 | Hueber |
| 6,081,735 A | 6/2000 | Diab et al. |
| 6,081,742 A | 6/2000 | Amano et al. |
| 6,083,157 A | 7/2000 | Noller |
| 6,083,172 A | 7/2000 | Baker, Jr. et al. |
| 6,088,607 A | 7/2000 | Diab et al. |
| 6,094,592 A | 7/2000 | Yorkey et al. |
| 6,095,974 A | 8/2000 | Shemwell et al. |
| 6,104,938 A | 8/2000 | Huiku et al. |
| 6,104,939 A | 8/2000 | Groner |
| 6,112,107 A | 8/2000 | Hannula |
| 6,113,541 A | 9/2000 | Dias et al. |
| 6,115,621 A | 9/2000 | Chin |
| 6,122,535 A | 9/2000 | Kaestle et al. |
| 6,133,994 A | 10/2000 | Mathews et al. |
| 6,135,952 A | 10/2000 | Coetzee |
| 6,144,444 A | 11/2000 | Haworth et al. |
| 6,144,867 A | 11/2000 | Walker et al. |
| 6,144,868 A | 11/2000 | Parker |
| 6,149,481 A | 11/2000 | Wang et al. |
| 6,150,951 A | 11/2000 | Olejniczak |
| 6,151,107 A | 11/2000 | Schöllermann et al. |
| 6,151,516 A | 11/2000 | Kiani-Azarbayjany et al. |
| 6,151,518 A | 11/2000 | Hayashi |
| 6,152,754 A | 11/2000 | Gerhardt et al. |
| 6,154,667 A | 11/2000 | Miura et al. |
| 6,157,850 A | 12/2000 | Diab et al. |
| 6,159,147 A | 12/2000 | Lichter |
| 6,163,715 A | 12/2000 | Larsen et al. |
| 6,165,005 A | 12/2000 | Mills et al. |
| 6,169,914 B1 | 1/2001 | Hovland et al. |
| 6,173,196 B1 | 1/2001 | Delonzor et al. |
| 6,178,343 B1 | 1/2001 | Bindszus et al. |
| 6,179,159 B1 | 1/2001 | Gurley |
| 6,181,958 B1 | 1/2001 | Steuer et al. |
| 6,181,959 B1 | 1/2001 | Schöllermann et al. |
| 6,184,521 B1 | 2/2001 | Coffin, IV et al. |
| 6,188,470 B1 | 2/2001 | Grace |
| 6,192,260 B1 | 2/2001 | Chance |
| 6,195,575 B1 | 2/2001 | Levinson |
| 6,198,951 B1 | 3/2001 | Kosuda et al. |
| 6,206,830 B1 | 3/2001 | Diab et al. |
| 6,213,952 B1 | 4/2001 | Finarov et al. |
| 6,217,523 B1 | 4/2001 | Amano et al. |
| 6,222,189 B1 | 4/2001 | Misner et al. |
| 6,223,064 B1 | 4/2001 | Lynn |
| 6,226,539 B1 | 5/2001 | Potratz |
| 6,226,540 B1 | 5/2001 | Bernreuter et al. |
| 6,229,856 B1 | 5/2001 | Diab et al. |
| 6,230,035 B1 | 5/2001 | Aoyagi et al. |
| 6,233,470 B1 | 5/2001 | Tsuchiya |
| 6,236,871 B1 | 5/2001 | Tsuchiya |
| 6,236,872 B1 | 5/2001 | Diab et al. |
| 6,240,305 B1 | 5/2001 | Tsuchiya |
| 6,253,097 B1 | 6/2001 | Aronow et al. |
| 6,253,098 B1 | 6/2001 | Walker et al. |
| 6,256,523 B1 | 7/2001 | Diab et al. |
| 6,256,524 B1 | 7/2001 | Walker et al. |
| 6,261,236 B1 | 7/2001 | Grimblatov |
| 6,263,221 B1 | 7/2001 | Chance et al. |
| 6,263,222 B1 | 7/2001 | Diab et al. |
| 6,263,223 B1 | 7/2001 | Shepherd et al. |
| 6,266,546 B1 | 7/2001 | Steuer et al. |
| 6,266,547 B1 | 7/2001 | Walker et al. |
| 6,272,363 B1 | 8/2001 | Casciani et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,894 B1 | 9/2001 | Oppelt et al. |
| 6,285,895 B1 | 9/2001 | Ristolainen et al. |
| 6,285,896 B1 | 9/2001 | Tobler et al. |
| 6,298,252 B1 | 10/2001 | Kovach et al. |
| 6,308,089 B1 | 10/2001 | Von der Ruhr et al. |

| | | | | | | |
|---|---|---|---|---|---|---|
| 6,321,100 | B1 | 11/2001 | Parker | 6,546,267 | B1 | 4/2003 | Sugiura et al. |
| 6,330,468 | B1 | 12/2001 | Scharf | 6,553,241 | B1 | 4/2003 | Mannheimer et al. |
| 6,334,065 | B1 | 12/2001 | Al-Ali et al. | 6,553,242 | B1 | 4/2003 | Sarussi |
| 6,339,715 | B1 | 1/2002 | Bahr et al. | 6,553,243 | B2 | 4/2003 | Gurley |
| 6,342,039 | B1 | 1/2002 | Lynn | 6,554,788 | B1 | 4/2003 | Hunley |
| 6,343,223 | B1 | 1/2002 | Chin et al. | 6,556,852 | B1 | 4/2003 | Schulze et al. |
| 6,343,224 | B1 | 1/2002 | Parker | 6,560,470 | B1 | 5/2003 | Pologe |
| 6,349,228 | B1 | 2/2002 | Kiani et al. | 6,564,077 | B2 | 5/2003 | Mortara |
| 6,351,658 | B1 | 2/2002 | Middleman et al. | 6,564,088 | B1 | 5/2003 | Soller et al. |
| 6,353,750 | B1 | 3/2002 | Kimura et al. | 6,571,113 | B1 | 5/2003 | Fein et al. |
| 6,356,774 | B1 | 3/2002 | Bernstein et al. | 6,571,114 | B1 | 5/2003 | Koike et al. |
| 6,360,113 | B1 | 3/2002 | Dettling | 6,574,491 | B2 | 6/2003 | Elghazzawi |
| 6,360,114 | B1 | 3/2002 | Diab et al. | 6,580,086 | B1 | 6/2003 | Schulz et al. |
| 6,361,501 | B1 | 3/2002 | Amano et al. | 6,584,336 | B1 | 6/2003 | Ali et al. |
| 6,363,269 | B1 | 3/2002 | Hanna et al. | 6,587,703 | B2 | 7/2003 | Cheng et al. |
| D455,834 | S | 4/2002 | Donars et al. | 6,587,704 | B1 | 7/2003 | Fine et al. |
| 6,370,408 | B1 | 4/2002 | Merchant et al. | 6,589,172 | B2 | 7/2003 | Williams et al. |
| 6,370,409 | B1 | 4/2002 | Chung et al. | 6,591,122 | B2 | 7/2003 | Schmitt |
| 6,374,129 | B1 | 4/2002 | Chin et al. | 6,591,123 | B2 | 7/2003 | Fein et al. |
| 6,377,829 | B1 | 4/2002 | Al-Ali et al. | 6,594,511 | B2 | 7/2003 | Stone et al. |
| 6,381,479 | B1 | 4/2002 | Norris | 6,594,512 | B1 | 7/2003 | Huang |
| 6,381,480 | B1 | 4/2002 | Stoddart et al. | 6,594,513 | B1 | 7/2003 | Jobsis et al. |
| 6,385,471 | B1 | 5/2002 | Mortz | 6,597,931 | B1 | 7/2003 | Cheng et al. |
| 6,385,821 | B1 | 5/2002 | Modgil et al. | 6,597,933 | B2 | 7/2003 | Kiani et al. |
| 6,388,240 | B2 | 5/2002 | Schulz et al. | 6,600,940 | B1 | 7/2003 | Fein et al. |
| 6,393,310 | B1 | 5/2002 | Kuenstner | 6,606,510 | B2 | 8/2003 | Swedlow et al. |
| 6,393,311 | B1 | 5/2002 | Edgar, Jr. et al. | 6,606,511 | B1 | 8/2003 | Ali et al. |
| 6,397,091 | B2 | 5/2002 | Diab et al. | 6,606,512 | B2 | 8/2003 | Muz et al. |
| 6,397,092 | B1 | 5/2002 | Norris et al. | 6,608,562 | B1 | 8/2003 | Kimura et al. |
| 6,397,093 | B1 | 5/2002 | Aldrich | 6,609,016 | B1 | 8/2003 | Lynn |
| 6,400,971 | B1 | 6/2002 | Finarov et al. | 6,615,064 | B1 | 9/2003 | Aldrich |
| 6,400,972 | B1 | 6/2002 | Fine | 6,615,065 | B1 | 9/2003 | Barrett et al. |
| 6,400,973 | B1 | 6/2002 | Winter | 6,618,602 | B2 | 9/2003 | Levin et al. |
| 6,402,690 | B1 | 6/2002 | Rhee et al. | 6,622,034 | B1 | 9/2003 | Gorski et al. |
| 6,408,198 | B1 | 6/2002 | Hanna et al. | 6,628,975 | B1 | 9/2003 | Fein et al. |
| 6,411,832 | B1 | 6/2002 | Guthermann | 6,631,281 | B1 | 10/2003 | Kästle |
| 6,411,833 | B1 | 6/2002 | Baker, Jr. et al. | 6,632,181 | B2 | 10/2003 | Flaherty |
| 6,419,671 | B1 | 7/2002 | Lemberg | 6,640,116 | B2 | 10/2003 | Diab |
| 6,421,549 | B1 | 7/2002 | Jacques | 6,643,530 | B2 | 11/2003 | Diab et al. |
| 6,430,423 | B2 | 8/2002 | DeLonzor et al. | 6,643,531 | B1 | 11/2003 | Katarow |
| 6,430,513 | B1 | 8/2002 | Wang et al. | 6,647,279 | B2 | 11/2003 | Pologe |
| 6,430,525 | B1 | 8/2002 | Weber et al. | 6,647,280 | B2 | 11/2003 | Bahr et al. |
| 6,434,408 | B1 | 8/2002 | Heckel et al. | 6,650,916 | B2 | 11/2003 | Cook |
| 6,438,396 | B1 | 8/2002 | Cook | 6,650,917 | B2 | 11/2003 | Diab et al. |
| 6,438,399 | B1 | 8/2002 | Kurth | 6,650,918 | B2 | 11/2003 | Terry |
| 6,449,501 | B1 | 9/2002 | Reuss | 6,654,621 | B2 | 11/2003 | Palatnik et al. |
| 6,453,183 | B1 | 9/2002 | Walker | 6,654,622 | B1 | 11/2003 | Eberhard et al. |
| 6,453,184 | B1 | 9/2002 | Hyogo et al. | 6,654,623 | B1 | 11/2003 | Kästle |
| 6,456,862 | B2 | 9/2002 | Benni | 6,654,624 | B2 | 11/2003 | Diab et al. |
| 6,461,305 | B1 | 10/2002 | Schnall | 6,658,276 | B2 | 12/2003 | Kianl et al. |
| 6,463,310 | B1 | 10/2002 | Swedlow et al. | 6,658,277 | B2 | 12/2003 | Wassermann |
| 6,463,311 | B1 | 10/2002 | Diab | 6,662,033 | B2 | 12/2003 | Casciani et al. |
| 6,466,808 | B1 | 10/2002 | Chin et al. | 6,665,551 | B1 | 12/2003 | Suzuki |
| 6,466,809 | B1 | 10/2002 | Riley | 6,668,182 | B2 | 12/2003 | Hubelbank |
| 6,470,199 | B1 | 10/2002 | Kopotic et al. | 6,668,183 | B2 | 12/2003 | Hicks et al. |
| 6,470,200 | B2 | 10/2002 | Walker et al. | 6,671,526 | B1 | 12/2003 | Aoyagi et al. |
| 6,480,729 | B2 | 11/2002 | Stone | 6,671,528 | B2 | 12/2003 | Steuer et al. |
| 6,490,466 | B1 | 12/2002 | Fein et al. | 6,671,530 | B2 | 12/2003 | Chung et al. |
| 6,493,568 | B1 | 12/2002 | Bell | 6,671,531 | B2 | 12/2003 | Al-Ali et al. |
| 6,496,711 | B1 | 12/2002 | Athan et al. | 6,671,532 | B1 | 12/2003 | Fudge et al. |
| 6,498,942 | B1 | 12/2002 | Esenaliev et al. | 6,675,031 | B1 | 1/2004 | Porges et al. |
| 6,501,974 | B2 | 12/2002 | Huiku | 6,678,543 | B2 | 1/2004 | Diab et al. |
| 6,501,975 | B2 | 12/2002 | Diab et al. | 6,681,126 | B2 | 1/2004 | Solenberger |
| 6,505,060 | B1 | 1/2003 | Norris | 6,681,128 | B2 | 1/2004 | Steuer et al. |
| 6,505,061 | B2 | 1/2003 | Larson | 6,681,454 | B2 | 1/2004 | Modgil et al. |
| 6,505,133 | B1 | 1/2003 | Hanna et al. | 6,684,090 | B2 | 1/2004 | Ali et al. |
| 6,510,329 | B2 | 1/2003 | Heckel | 6,684,091 | B2 | 1/2004 | Parker |
| 6,510,331 | B1 | 1/2003 | Williams et al. | 6,694,160 | B2 | 2/2004 | Chin |
| 6,512,937 | B2 | 1/2003 | Blank et al. | 6,697,653 | B2 | 2/2004 | Hanna |
| 6,515,273 | B2 | 2/2003 | Al-Ali | 6,697,655 | B2 | 2/2004 | Sueppel et al. |
| 6,519,484 | B1 | 2/2003 | Lovejoy et al. | 6,697,656 | B1 | 2/2004 | Al-Ali |
| 6,519,486 | B1 | 2/2003 | Edgar, Jr. et al. | 6,697,658 | B2 | 2/2004 | Al-Ali |
| 6,519,487 | B1 | 2/2003 | Parker | RE38,476 | E | 3/2004 | Diab et al. |
| 6,525,386 | B1 | 2/2003 | Mills et al. | 6,699,194 | B1 | 3/2004 | Diab et al. |
| 6,526,300 | B1 | 2/2003 | Kiani et al. | 6,699,199 | B2 | 3/2004 | Asada et al. |
| 6,526,301 | B2 | 2/2003 | Larsen et al. | 6,701,170 | B2 | 3/2004 | Stetson |
| 6,532,958 | B1 | 3/2003 | Buan et al. | 6,702,752 | B2 | 3/2004 | Dekker |
| 6,541,756 | B2 | 4/2003 | Schulz et al. | 6,707,257 | B2 | 3/2004 | Norris |
| 6,542,764 | B1 | 4/2003 | Al-Ali et al. | 6,708,049 | B1 | 3/2004 | Berson et al. |

| | | |
|---|---|---|
| 6,709,402 B2 | 3/2004 | Dekker |
| 6,711,424 B1 | 3/2004 | Fine et al. |
| 6,711,425 B1 | 3/2004 | Reuss |
| 6,712,762 B1 | 3/2004 | Lichter |
| 6,714,803 B1 | 3/2004 | Mortz |
| 6,714,804 B2 | 3/2004 | Al-Ali et al. |
| 6,714,805 B2 | 3/2004 | Jeon et al. |
| RE38,492 E | 4/2004 | Diab et al. |
| 6,719,686 B2 | 4/2004 | Coakley et al. |
| 6,719,705 B2 | 4/2004 | Mills |
| 6,720,734 B2 | 4/2004 | Norris |
| 6,721,584 B2 | 4/2004 | Baker, Jr. et al. |
| 6,721,585 B1 | 4/2004 | Parker |
| 6,725,074 B1 | 4/2004 | Kästle |
| 6,725,075 B2 | 4/2004 | Al-Ali |
| 6,731,962 B1 | 5/2004 | Katarow |
| 6,731,963 B2 | 5/2004 | Finarov et al. |
| 6,731,967 B1 | 5/2004 | Turcott |
| 6,735,459 B2 | 5/2004 | Parker |
| 6,745,060 B2 | 6/2004 | Diab et al. |
| 6,745,061 B1 | 6/2004 | Hicks et al. |
| 6,748,253 B2 | 6/2004 | Norris et al. |
| 6,748,254 B2 | 6/2004 | ONeill et al. |
| 6,754,515 B1 | 6/2004 | Pologe |
| 6,754,516 B2 | 6/2004 | Mannheimer |
| 6,760,607 B2 | 7/2004 | Al-All |
| 6,760,609 B2 | 7/2004 | Jacques |
| 6,760,610 B2 | 7/2004 | Tschupp et al. |
| 6,763,255 B2 | 7/2004 | DeLonzor et al. |
| 6,763,256 B2 | 7/2004 | Kimball et al. |
| 6,770,028 B1 | 8/2004 | Ali et al. |
| 6,771,994 B2 | 8/2004 | Kiani et al. |
| 6,773,397 B2 | 8/2004 | Kelly |
| 6,778,923 B2 | 8/2004 | Norris et al. |
| 6,780,158 B2 | 8/2004 | Yarita |
| 6,791,689 B1 | 9/2004 | Weckstrom |
| 6,792,300 B1 | 9/2004 | Diab et al. |
| 6,793,654 B2 | 9/2004 | Lemberg |
| 6,801,797 B2 | 10/2004 | Mannheimer et al. |
| 6,801,798 B2 | 10/2004 | Geddes et al. |
| 6,801,799 B2 | 10/2004 | Mendelson |
| 6,801,802 B2 | 10/2004 | Sitzman et al. |
| 6,802,812 B1 | 10/2004 | Walker et al. |
| 6,805,673 B2 | 10/2004 | Dekker |
| 6,810,277 B2 | 10/2004 | Edgar, Jr. et al. |
| 6,813,511 B2 | 11/2004 | Diab et al. |
| 6,816,266 B2 | 11/2004 | Varshneya et al. |
| 6,816,741 B2 | 11/2004 | Diab |
| 6,819,950 B2 | 11/2004 | Mills |
| 6,822,564 B2 | 11/2004 | Al-Ali |
| 6,825,619 B2 | 11/2004 | Norris |
| 6,826,419 B2 | 11/2004 | Diab et al. |
| 6,829,496 B2 | 12/2004 | Nagai et al. |
| 6,830,711 B2 | 12/2004 | Mills et al. |
| 6,836,679 B2 | 12/2004 | Baker, Jr. et al. |
| 6,839,579 B1 | 1/2005 | Chin |
| 6,839,580 B2 | 1/2005 | Zonios et al. |
| 6,839,582 B2 | 1/2005 | Heckel |
| 6,839,659 B2 | 1/2005 | Tarassenko et al. |
| 6,842,635 B1 | 1/2005 | Parker |
| 6,845,256 B2 | 1/2005 | Chin et al. |
| 6,850,787 B2 | 2/2005 | Weber et al. |
| 6,850,788 B2 | 2/2005 | Al-Ali |
| 6,850,789 B2 | 2/2005 | Schweitzer, Jr. et al. |
| 6,861,639 B2 | 3/2005 | Al-Ali |
| 6,863,652 B2 | 3/2005 | Huang et al. |
| 6,865,407 B2 | 3/2005 | Kimball et al. |
| 6,879,850 B2 | 4/2005 | Kimball |
| 6,882,874 B2 | 4/2005 | Huiku |
| 6,889,153 B2 | 5/2005 | Dietiker |
| 6,898,452 B2 | 5/2005 | Al-Ali et al. |
| 6,909,912 B2 | 6/2005 | Melker et al. |
| 6,912,413 B2 | 6/2005 | Rantala et al. |
| 6,916,289 B2 | 7/2005 | Schnall |
| 6,920,345 B2 | 7/2005 | Al-Ali et al. |
| 6,931,269 B2 | 8/2005 | Terry |
| 6,934,570 B2 | 8/2005 | Kiani et al. |
| 6,939,307 B1 | 9/2005 | Dunlop |
| 6,941,162 B2 | 9/2005 | Fudge et al. |
| 6,947,781 B2 | 9/2005 | Asada et al. |
| 6,950,687 B2 | 9/2005 | Al-Ali |
| 6,954,664 B2 | 10/2005 | Sweitzer |
| 6,963,767 B2 | 11/2005 | Rantala et al. |
| 6,967,652 B1 | 11/2005 | Nubling et al. |
| 6,968,221 B2 | 11/2005 | Rosenthal |
| 6,971,580 B2 | 12/2005 | DeLonzor et al. |
| 6,979,812 B2 | 12/2005 | Al-Ali |
| 6,983,178 B2 | 1/2006 | Fine et al. |
| 6,985,763 B2 | 1/2006 | Boas et al. |
| 6,985,764 B2 | 1/2006 | Mason et al. |
| 6,990,426 B2 | 1/2006 | Yoon et al. |
| 6,992,751 B2 | 1/2006 | Al-Ali |
| 6,992,772 B2 | 1/2006 | Block et al. |
| 6,993,371 B2 | 1/2006 | Kiani et al. |
| 6,993,372 B2 | 1/2006 | Fine et al. |
| 6,996,427 B2 | 2/2006 | Ali et al. |
| 6,999,809 B2 | 2/2006 | Currier et al. |
| 7,003,338 B2 | 2/2006 | Weber et al. |
| 7,003,339 B2 | 2/2006 | Diab et al. |
| 7,006,855 B1 | 2/2006 | Sarussi |
| 7,006,856 B2 | 2/2006 | Baker, Jr. et al. |
| 7,016,715 B2 | 3/2006 | Stetson |
| 7,020,507 B2 | 3/2006 | Scharf et al. |
| 7,024,233 B2 | 4/2006 | Ali et al. |
| 7,024,235 B2 | 4/2006 | Melker et al. |
| 7,025,728 B2 | 4/2006 | Ito et al. |
| 7,027,849 B2 | 4/2006 | Al-Ali et al. |
| 7,027,850 B2 | 4/2006 | Wasserman |
| 7,035,697 B1 | 4/2006 | Brown |
| 7,039,449 B2 | 5/2006 | Al-Ali |
| 7,043,289 B2 | 5/2006 | Fine et al. |
| 7,047,055 B2 | 5/2006 | Boas et al. |
| 7,047,056 B2 | 5/2006 | Hannula et al. |
| 7,048,687 B1 | 5/2006 | Reuss et al. |
| 7,060,035 B2 | 6/2006 | Wasserman et al. |
| 7,062,307 B2 | 6/2006 | Norris et al. |
| 7,067,893 B2 | 6/2006 | Mills et al. |
| 7,072,701 B2 | 7/2006 | Chen et al. |
| 7,072,702 B2 | 7/2006 | Edgar, Jr. et al. |
| 7,079,880 B2 | 7/2006 | Stetson |
| 7,085,597 B2 | 8/2006 | Fein et al. |
| 7,096,052 B2 | 8/2006 | Mason et al. |
| 7,096,054 B2 | 8/2006 | Abdul-Hafiz et al. |
| 7,107,088 B2 | 9/2006 | Aceti |
| 7,113,815 B2 | 9/2006 | O'Neil et al. |
| 7,123,950 B2 | 10/2006 | Mannheimer |
| 7,127,278 B2 | 10/2006 | Melker et al. |
| 7,130,671 B2 | 10/2006 | Baker, Jr. et al. |
| 7,132,641 B2 | 11/2006 | Schulz et al. |
| 7,133,711 B2 | 11/2006 | Chernoguz et al. |
| 7,139,599 B2 | 11/2006 | Terry |
| 7,142,901 B2 | 11/2006 | Kiani et al. |
| 7,161,484 B2 | 1/2007 | Tsoukalis |
| 7,162,288 B2 | 1/2007 | Nordstrom |
| 7,190,987 B2 | 3/2007 | Lindekugel et al. |
| 7,198,778 B2 | 4/2007 | Achilefu et al. |
| 7,204,250 B1 | 4/2007 | Burton |
| 7,209,775 B2 | 4/2007 | Bae et al. |
| 7,215,984 B2 | 5/2007 | Diab et al. |
| 7,225,006 B2 | 5/2007 | Al-Ali et al. |
| 7,228,161 B2 | 6/2007 | Chin |
| 7,236,811 B2 | 6/2007 | Schmitt |
| 7,236,881 B2 | 6/2007 | Liu et al. |
| 7,238,159 B2 | 7/2007 | Banet et al. |
| 7,248,910 B2 | 7/2007 | Li et al. |
| 7,254,433 B2 | 8/2007 | Diab et al. |
| 7,254,434 B2 | 8/2007 | Schulz et al. |
| 7,263,395 B2 | 8/2007 | Chan et al. |
| 7,272,426 B2 | 9/2007 | Schmid |
| 7,280,858 B2 | 10/2007 | Al-Ali et al. |
| 7,295,866 B2 | 11/2007 | Al-Ali et al. |
| 7,305,262 B2 | 12/2007 | Brodnick et al. |
| 7,315,753 B2 | 1/2008 | Baker, Jr. et al. |
| 7,392,074 B2 | 6/2008 | Isaacson et al. |
| 7,438,687 B2 | 10/2008 | Lewicke |
| 2001/0021803 A1 | 9/2001 | Blank et al. |
| 2001/0051767 A1 | 12/2001 | Williams et al. |
| 2002/0016537 A1 | 2/2002 | Muz et al. |

| | | |
|---|---|---|
| 2002/0026109 A1 | 2/2002 | Diab et al. |
| 2002/0028990 A1 | 3/2002 | Sheperd et al. |
| 2002/0038078 A1 | 3/2002 | Ito |
| 2002/0042558 A1 | 4/2002 | Mendelson |
| 2002/0068859 A1 | 6/2002 | Knopp |
| 2002/0072681 A1 | 6/2002 | Schnall |
| 2002/0116797 A1 | 8/2002 | Modgil et al. |
| 2002/0128544 A1 | 9/2002 | Diab et al. |
| 2002/0133067 A1 | 9/2002 | Jackson, III |
| 2002/0156354 A1 | 10/2002 | Larson |
| 2002/0173706 A1 | 11/2002 | Takatani |
| 2002/0173709 A1 | 11/2002 | Fine et al. |
| 2002/0190863 A1 | 12/2002 | Lynn |
| 2002/0198442 A1 | 12/2002 | Rantala et al. |
| 2003/0018243 A1 | 1/2003 | Gerhardt et al. |
| 2003/0036690 A1 | 2/2003 | Geddes et al. |
| 2003/0045785 A1 | 3/2003 | Diab et al. |
| 2003/0073889 A1 | 4/2003 | Keilbach et al. |
| 2003/0073890 A1 | 4/2003 | Hanna |
| 2003/0100840 A1 | 5/2003 | Sugiura et al. |
| 2003/0132495 A1 | 7/2003 | Mills et al. |
| 2003/0135099 A1 | 7/2003 | Al-Ali |
| 2003/0162414 A1 | 8/2003 | Schulz et al. |
| 2003/0171662 A1 | 9/2003 | O'Connor et al. |
| 2003/0176776 A1 | 9/2003 | Huiku |
| 2003/0181799 A1 | 9/2003 | Lindekugel et al. |
| 2003/0187337 A1 | 10/2003 | Tarassenko et al. |
| 2003/0195402 A1 | 10/2003 | Fein et al. |
| 2003/0197679 A1 | 10/2003 | Ali et al. |
| 2003/0212316 A1 | 11/2003 | Leiden et al. |
| 2003/0225323 A1 | 12/2003 | Kiani et al. |
| 2003/0225337 A1 | 12/2003 | Scharf et al. |
| 2003/0236452 A1 | 12/2003 | Melker et al. |
| 2003/0236647 A1 | 12/2003 | Yoon et al. |
| 2004/0006261 A1 | 1/2004 | Swedlow et al. |
| 2004/0010188 A1 | 1/2004 | Wasserman et al. |
| 2004/0024297 A1 | 2/2004 | Chen et al. |
| 2004/0024326 A1 | 2/2004 | Yeo et al. |
| 2004/0034293 A1 | 2/2004 | Kimball |
| 2004/0039272 A1 | 2/2004 | Abdul-Hafiz et al. |
| 2004/0039273 A1 | 2/2004 | Terry |
| 2004/0054269 A1 | 3/2004 | Rantala et al. |
| 2004/0054291 A1 | 3/2004 | Schulz et al. |
| 2004/0059209 A1 | 3/2004 | Al-Ali et al. |
| 2004/0059210 A1 | 3/2004 | Stetson |
| 2004/0064020 A1 | 4/2004 | Diab et al. |
| 2004/0068164 A1 | 4/2004 | Diab et al. |
| 2004/0087846 A1 | 5/2004 | Wasserman |
| 2004/0092805 A1 | 5/2004 | Yarita |
| 2004/0097797 A1 | 5/2004 | Porges et al. |
| 2004/0098009 A1 | 5/2004 | Boecker et al. |
| 2004/0107065 A1 | 6/2004 | Al-Ali et al. |
| 2004/0116788 A1 | 6/2004 | Chernoguz et al. |
| 2004/0116789 A1 | 6/2004 | Boas et al. |
| 2004/0117891 A1 | 6/2004 | Hannula et al. |
| 2004/0122300 A1 | 6/2004 | Boas et al. |
| 2004/0122302 A1 | 6/2004 | Mason et al. |
| 2004/0133087 A1 | 7/2004 | Ali et al. |
| 2004/0133088 A1 | 7/2004 | Al-Ali et al. |
| 2004/0138538 A1 | 7/2004 | Stetson |
| 2004/0138540 A1 | 7/2004 | Baker, Jr. et al. |
| 2004/0143172 A1 | 7/2004 | Fudge et al. |
| 2004/0147821 A1 | 7/2004 | Al-Ali et al. |
| 2004/0147822 A1 | 7/2004 | Al-Ali et al. |
| 2004/0147823 A1 | 7/2004 | Kiani et al. |
| 2004/0147824 A1 | 7/2004 | Diab et al. |
| 2004/0152965 A1 | 8/2004 | Diab et al. |
| 2004/0158134 A1 | 8/2004 | Diab et al. |
| 2004/0158135 A1 | 8/2004 | Baker, Jr. et al. |
| 2004/0162472 A1 | 8/2004 | Berson et al. |
| 2004/0167381 A1 | 8/2004 | Lichter |
| 2004/0171920 A1 | 9/2004 | Mannheimer et al. |
| 2004/0171948 A1 | 9/2004 | Terry |
| 2004/0176671 A1 | 9/2004 | Fine et al. |
| 2004/0181133 A1 | 9/2004 | Al-Ali et al. |
| 2004/0181134 A1 | 9/2004 | Baker, Jr. et al. |
| 2004/0186358 A1 | 9/2004 | Chernow et al. |
| 2004/0199063 A1 | 10/2004 | O'Neil et al. |
| 2004/0204636 A1 | 10/2004 | Diab et al. |
| 2004/0204637 A1 | 10/2004 | Diab et al. |
| 2004/0204638 A1 | 10/2004 | Diab et al. |
| 2004/0204639 A1 | 10/2004 | Casciani et al. |
| 2004/0204865 A1 | 10/2004 | Lee et al. |
| 2004/0210146 A1 | 10/2004 | Diab et al. |
| 2004/0215069 A1 | 10/2004 | Mannheimer |
| 2004/0215085 A1 | 10/2004 | Schnall |
| 2004/0230107 A1 | 11/2004 | Asada et al. |
| 2004/0230108 A1 | 11/2004 | Melker et al. |
| 2004/0236196 A1 | 11/2004 | Diab et al. |
| 2004/0242980 A1 | 12/2004 | Kiani et al. |
| 2004/0249252 A1 | 12/2004 | Fine et al. |
| 2004/0257557 A1 | 12/2004 | Block et al. |
| 2004/0260161 A1 | 12/2004 | Melker et al. |
| 2004/0267103 A1 | 12/2004 | Li et al. |
| 2004/0267104 A1 | 12/2004 | Hannula et al. |
| 2004/0267140 A1 | 12/2004 | Ito et al. |
| 2005/0004479 A1 | 1/2005 | Townsend et al. |
| 2005/0010092 A1 | 1/2005 | Weber et al. |
| 2005/0014999 A1 | 1/2005 | Rahe-Meyer |
| 2005/0017864 A1 | 1/2005 | Tsoukalis et al. |
| 2005/0020887 A1 | 1/2005 | Goldberg |
| 2005/0020894 A1 | 1/2005 | Norris et al. |
| 2005/0033128 A1 | 2/2005 | Ali et al. |
| 2005/0033129 A1 | 2/2005 | Edgar, Jr. et al. |
| 2005/0033131 A1 | 2/2005 | Chen |
| 2005/0043599 A1 | 2/2005 | O'Mara |
| 2005/0043600 A1 | 2/2005 | Diab et al. |
| 2005/0043763 A1 | 2/2005 | Marcovecchio et al. |
| 2005/0049468 A1 | 3/2005 | Carlson |
| 2005/0049470 A1 | 3/2005 | Terry |
| 2005/0049471 A1 | 3/2005 | Aceti |
| 2005/0070773 A1 | 3/2005 | Chin |
| 2005/0075546 A1 | 4/2005 | Samsoondar |
| 2005/0075550 A1 | 4/2005 | Lindekugel |
| 2005/0085704 A1 | 4/2005 | Schulz |
| 2005/0090720 A1 | 4/2005 | Wu |
| 2005/0113704 A1 | 5/2005 | Lawson et al. |
| 2005/0177034 A1 | 8/2005 | Beaumont |
| 2005/0197548 A1 | 9/2005 | Dietiker |
| 2005/0228248 A1 | 10/2005 | Dietiker |
| 2005/0228299 A1 | 10/2005 | Banet et al. |
| 2005/0228300 A1 | 10/2005 | Jaime et al. |
| 2005/0256386 A1 | 11/2005 | Chan |
| 2005/0268916 A1 | 12/2005 | Mumford et al. |
| 2005/0272986 A1 | 12/2005 | Smith |
| 2005/0277819 A1 | 12/2005 | Kiani et al. |
| 2005/0283059 A1 | 12/2005 | Iyer et al. |
| 2006/0020179 A1 | 1/2006 | Anderson |
| 2006/0025660 A1 | 2/2006 | Swedlow et al. |
| 2006/0030762 A1 | 2/2006 | David et al. |
| 2006/0030764 A1 | 2/2006 | Porges |
| 2006/0030765 A1 | 2/2006 | Swedlow et al. |
| 2006/0058594 A1 | 3/2006 | Ishizuka et al. |
| 2006/0074280 A1 | 4/2006 | Martis |
| 2006/0084852 A1 | 4/2006 | Mason et al. |
| 2006/0084878 A1 | 4/2006 | Banet |
| 2006/0089547 A1 | 4/2006 | Sarussi |
| 2006/0106294 A1 | 5/2006 | Maser et al. |
| 2006/0122517 A1 | 6/2006 | Banet |
| 2006/0129039 A1 | 6/2006 | Lindner |
| 2006/0155198 A1 | 7/2006 | Schmid |
| 2006/0161054 A1 | 7/2006 | Reuss et al. |
| 2006/0167351 A1 | 7/2006 | Isaacson et al. |
| 2006/0173257 A1 | 8/2006 | Nagai |
| 2006/0195028 A1 | 8/2006 | Hannula et al. |
| 2006/0211932 A1 | 9/2006 | Al-Ali et al. |
| 2006/0224058 A1 | 10/2006 | Mannheimer |
| 2006/0238358 A1 | 10/2006 | Al-Ali et al. |
| 2006/0247501 A1 | 11/2006 | Ali |
| 2006/0258921 A1 | 11/2006 | Addison et al. |
| 2007/0032710 A1 | 2/2007 | Raridan et al. |
| 2007/0032712 A1 | 2/2007 | Raridan et al. |
| 2007/0032715 A1 | 2/2007 | Eghbal et al. |
| 2007/0060808 A1 | 3/2007 | Hoarau |
| 2007/0073117 A1 | 3/2007 | Raridan |
| 2007/0073121 A1 | 3/2007 | Hoarau et al. |
| 2007/0073122 A1 | 3/2007 | Hoarau |
| 2007/0073123 A1 | 3/2007 | Raridan |

| | | | | | | |
|---|---|---|---|---|---|---|
| 2007/0073125 | A1 | 3/2007 | Hoarau et al. | JP | 06 014906 | 1/1994 |
| 2007/0073126 | A1 | 3/2007 | Raridan, Jr. | JP | 06014906 | 1/1994 |
| 2007/0073128 | A1 | 3/2007 | Hoarau | JP | 6016774 | 3/1994 |
| 2007/0078315 | A1 | 4/2007 | Kling et al. | JP | 3116255 | 4/1994 |
| 2007/0078316 | A1 | 4/2007 | Hoarau | JP | 6029504 | 4/1994 |
| 2007/0208235 | A1 | 9/2007 | Besson et al. | JP | 6098881 | 4/1994 |
| 2007/0208269 | A1 | 9/2007 | Mumford et al. | JP | 06 154177 | 6/1994 |
| 2007/0260129 | A1 | 11/2007 | Chin | JP | 6269430 | 9/1994 |
| 2007/0260130 | A1 | 11/2007 | Chin | JP | 6285048 | 10/1994 |
| 2007/0260131 | A1 | 11/2007 | Chin | JP | 7001273 | 1/1995 |
| 2007/0299328 | A1 | 12/2007 | Chin et al. | JP | 7124138 | 5/1995 |
| 2008/0230363 | A1 | 9/2008 | Yang et al. | JP | 7136150 | 5/1995 |
| | | | | JP | 3116259 | 6/1995 |

FOREIGN PATENT DOCUMENTS

| | | | | | |
|---|---|---|---|---|---|
| DE | 3516338 | 11/1986 | JP | 3116260 | 6/1995 |
| DE | 37 03 458 | 8/1988 | JP | 7155311 | 6/1995 |
| DE | 3938759 | 5/1991 | JP | 7155313 | 6/1995 |
| DE | 4210102 | 9/1993 | JP | 3238813 | 7/1995 |
| DE | 4423597 | 8/1995 | JP | 7171139 | 7/1995 |
| DE | 19632361 | 2/1997 | JP | 3134144 | 9/1995 |
| DE | 69123448 | 5/1997 | JP | 7236625 | 9/1995 |
| DE | 19703220 | 7/1997 | JP | 7246191 | 9/1995 |
| DE | 19640807 | 9/1997 | JP | 8256996 | 10/1996 |
| DE | 19647877 | 4/1998 | JP | 9192120 | 7/1997 |
| DE | 10030862 | 1/2002 | JP | 10216113 | 8/1998 |
| DE | 20318882 | 4/2004 | JP | 10216114 | 8/1998 |
| EP | 0127947 | 5/1984 | JP | 10216115 | 8/1998 |
| EP | 00194105 | 9/1986 | JP | 10337282 | 12/1998 |
| EP | 00204459 | 12/1986 | JP | 11019074 | 1/1999 |
| EP | 0 262 779 | 4/1988 | JP | 11155841 | 6/1999 |
| EP | 0315040 | 10/1988 | JP | 11 188019 | 7/1999 |
| EP | 0314331 | 5/1989 | JP | 11244268 | 9/1999 |
| EP | 00352923 | 1/1990 | JP | 20107157 | 4/2000 |
| EP | 0 360 977 | 4/1990 | JP | 20237170 | 9/2000 |
| EP | 00430340 | 6/1991 | JP | 21245871 | 9/2001 |
| EP | 0435 500 | 7/1991 | JP | 22224088 | 8/2002 |
| EP | 0572684 | 5/1992 | JP | 22282242 | 10/2002 |
| EP | 00497021 | 8/1992 | JP | 23153881 | 5/2003 |
| EP | 0529412 | 8/1992 | JP | 23153882 | 5/2003 |
| EP | 0531631 | 9/1992 | JP | 23169791 | 6/2003 |
| EP | 0566354 | 4/1993 | JP | 23194714 | 7/2003 |
| EP | 0587009 | 8/1993 | JP | 23210438 | 7/2003 |
| EP | 00630203 | 9/1993 | JP | 23275192 | 9/2003 |
| EP | 0 572 684 | 12/1993 | JP | 23339678 | 12/2003 |
| EP | 00615723 | 9/1994 | JP | 24008572 | 1/2004 |
| EP | 00702931 | 3/1996 | JP | 24089546 | 3/2004 |
| EP | 00724860 | 8/1996 | JP | 24113353 | 4/2004 |
| EP | 00793942 | 9/1997 | JP | 24135854 | 5/2004 |
| EP | 0 864 293 | 9/1998 | JP | 24148069 | 5/2004 |
| EP | 01006863 | 10/1998 | JP | 24148070 | 5/2004 |
| EP | 01006864 | 10/1998 | JP | 2459810 | 6/2004 |
| EP | 0875199 | 11/1998 | JP | 24166775 | 6/2004 |
| EP | 00998214 | 12/1998 | JP | 24194908 | 7/2004 |
| EP | 0 898 933 | 3/1999 | JP | 24202190 | 7/2004 |
| EP | 0898933 | 3/1999 | JP | 24248819 | 9/2004 |
| EP | 01332713 | 8/2003 | JP | 24248820 | 9/2004 |
| EP | 01469773 | 8/2003 | JP | 24261364 | 9/2004 |
| EP | 1502529 | 7/2004 | JP | 24290412 | 10/2004 |
| EP | 01491135 | 12/2004 | JP | 24290544 | 10/2004 |
| FR | 2685865 | 1/1992 | JP | 24290545 | 10/2004 |
| GB | 2 259 545 | 3/1993 | JP | 24329406 | 11/2004 |
| JP | 63275325 | 11/1988 | JP | 24329607 | 11/2004 |
| JP | 2013450 | 1/1990 | JP | 24329928 | 11/2004 |
| JP | 2111343 | 4/1990 | JP | 24337605 | 12/2004 |
| JP | 02 191434 | 7/1990 | JP | 24344367 | 12/2004 |
| JP | 2237544 | 9/1990 | JP | 24351107 | 12/2004 |
| JP | 03 173536 | 7/1991 | JP | 25034472 | 2/2005 |
| JP | 3170866 | 7/1991 | WO | WO 98/09566 | 10/1989 |
| JP | 3245042 | 10/1991 | WO | WO 90/01293 | 2/1990 |
| JP | 4174648 | 6/1992 | WO | WO 90/04352 | 5/1990 |
| JP | 4191642 | 7/1992 | WO | WO 91/01678 | 2/1991 |
| JP | 4332536 | 11/1992 | WO | WO 91/11137 | 8/1991 |
| JP | 3124073 | 3/1993 | WO | WO 92/00513 | 1/1992 |
| JP | 5049624 | 3/1993 | WO | WO 92/21281 | 12/1992 |
| JP | 5049625 | 3/1993 | WO | WO 93/09711 | 5/1993 |
| JP | 3115374 | 4/1993 | WO | WO 93/13706 | 7/1993 |
| JP | 05 200031 | 8/1993 | WO | WO 93/16629 | 9/1993 |
| JP | 2005/200031 | 8/1993 | WO | WO 94/03102 | 2/1994 |
| JP | 5212016 | 8/1993 | WO | WO 94/23643 | 10/1994 |
| | | | WO | WO 95/02358 | 1/1995 |

| | | |
|---|---|---|
| WO | WO 95/12349 | 5/1995 |
| WO | WO 95/16970 | 6/1995 |
| WO | WO 96/13208 | 5/1996 |
| WO | WO 96/39927 | 12/1996 |
| WO | WO 97/36536 | 10/1997 |
| WO | WO 97/36538 | 10/1997 |
| WO | WO 97/49330 | 12/1997 |
| WO | WO 98/17174 | 4/1998 |
| WO | WO 98/18382 | 5/1998 |
| WO | WO 98/43071 | 10/1998 |
| WO | WO 98/51212 | 11/1998 |
| WO | WO 98/57577 | 12/1998 |
| WO | WO 99/00053 | 1/1999 |
| WO | WO 99/32030 | 7/1999 |
| WO | WO 99/47039 | 9/1999 |
| WO | WO 99/63884 | 12/1999 |
| WO | WO 00/21438 | 4/2000 |
| WO | WO 00/28888 | 5/2000 |
| WO | WO 00/59374 | 10/2000 |
| WO | WO 01/13790 | 3/2001 |
| WO | WO 01/16577 | 3/2001 |
| WO | WO 01/17421 | 3/2001 |
| WO | WO 01/47426 | 3/2001 |
| WO | WO 01/40776 | 6/2001 |
| WO | WO 01/67946 | 9/2001 |
| WO | WO 01/76461 | 10/2001 |
| WO | WO 02/14793 | 2/2002 |
| WO | WO 02/35999 | 5/2002 |
| WO | WO 02/062213 | 8/2002 |
| WO | WO 02/074162 | 9/2002 |
| WO | WO 02/085202 | 10/2002 |
| WO | WO 03/000125 | 1/2003 |
| WO | WO 03/001180 | 1/2003 |
| WO | WO 03/009750 | 2/2003 |
| WO | WO 03/011127 | 2/2003 |
| WO | WO 03/020129 | 3/2003 |
| WO | WO 03/039326 | 5/2003 |
| WO | WO 03/063697 | 8/2003 |
| WO | WO 03/073924 | 9/2003 |
| WO | WO 04/000114 | 12/2003 |
| WO | WO 2004/006748 | 1/2004 |
| WO | WO 2004/069046 | 8/2004 |
| WO | WO 2004/075746 | 9/2004 |
| WO | WO 2005/002434 | 1/2005 |
| WO | WO 2005/009221 | 2/2005 |
| WO | WO 2005/010567 | 2/2005 |
| WO | WO 2005/010568 | 2/2005 |
| WO | WO 2005/020120 | 3/2005 |
| WO | WO 2005/065540 | 7/2005 |
| WO | WO2006006158 | 1/2006 |

OTHER PUBLICATIONS

Zahar, N., et al.; "Automatic Feedback Control of Oxygen Therapy Using Pulse Oximetry," *Annual International Conference of the IEEE Engineering in Medicine and Biology Society*, vol. 13, No. 4, pp. 1614-1615 (1991).

Aoyagi, T., et al.; "Analysis of Motion Artifacts in Pulse Oximetry," *Japanese Society ME*, vol. 42, p. 20 (1993) (Article in Japanese—contains English summary of article).

Barreto, A.B., et al.; "Adaptive Cancelation of Motion artifact in Photoplethysmographic Blood Volume Pulse Measurements for Exercise Evaluation," *IEEE-EMBC and CMBEC—Theme 4: Signal Processing*, pp. 983-984 (1995).

Vincente, L.M., et al.; "Adaptive Pre-Processing of Photoplethysmographic Blood Volume Pulse Measurements," pp. 114-117 (1996).

Plummer, John L., et al.; "Identification of Movement Artifact by the Nellcor N-200 and N-3000 Pulse Oximeters," *Journal of clinical Monitoring*, vol. 13, pp. 109-113 (1997).

Barnum, P.T., et al.; "Novel Pulse Oximetry Technology Capable of Reliable Bradycardia Monitoring in the Neonate," *Respiratory Care*, vol. 42, No. 1, p. 1072 (Nov. 1997).

Poets, C. F., et al.; "Detection of movement artifact in recorded pulse oximeter saturation," *Eur. J. Pediatr.*; vol. 156, pp. 808-811 (1997).

Masin, Donald I., et al.; "Fetal Transmission Pulse Oximetry," *Proceedings 19th International Conference IEEE/EMBS*, Oct. 30th-Nov. 2, 1997; pp. 2326-2329.

Block, Frank E., Jr., et al.; "Technology evaluation report: Obtaining pulse oximeter signals when the usual probe cannot be used," *International journal of clinical Monitoring and Computing*, vol. 14, pp. 23-28 (1997).

Nijland, Roel, et al.; "Validation of Reflectance Pulse Oximetry: An Evaluation of a new Sensor in Piglets," *Journal of Clinical Monitoring*, vol. 13, pp. 43-49 (1997).

Soto, Denise A.; "A Comparative Study of Pulse Oximeter Measurements: Digit Versus Earlobe," Master of Science Thesis, California State University Dominguez Hills, May 1997, 46 pgs.

Faisst, Karin, et al.; "Intrapartum Reflectance Pulse Oximetry: Effects of Sensor Location and Fixation Duration on Oxygen Saturation Readings," *Journal of Clinical Monitoring*, vol. 13, pp. 299-302 (1997).

Izumi, Akio, et al.; "Accuracy and Utility of a New Reflectance Pulse Oximeter for Fetal Monitoring During Labor," *Journal of Clinical Monitoring*, vol. 13, pp. 103-108 (1997).

Mannheimer, Paul D., et al.; "Wavelength Selection for Low-Saturation Pulse Oximetry," *IEEE Transactions on Biomedical Engineering*, vol. 44, No. 3, pp. 148-158 (Mar. 1997).

"Smaller Product, Tighter Tolerances Pose Dispensing Challenges for Medical Device Manufacturer," *Adhesives Age*, pp. 40-41 (Oct. 1997).

Buschman, J.P., et al.; "Principles and Problems of Calibration of Fetal Oximeters," *Biomedizinische Technik*, vol. 42, pp. 265-266 (1997).

Pickett, John, et al.; "Pulse Oximetry and PPG Measurements in Plastic Surgery," *Proceedings—19th International Conference—IEEE/EMBS*, Chicago, Illinois, Oct. 30-Nov. 2, 1997, pp. 2330-2332.

Leahy, Martin J., et al.; "Sensor Validation in Biomedical Applications," *IFAC Modelling and Control in Biomedical Systems*, Warwick, UK; pp. 221-226 (1997).

Barreto, Armando B., et al.; "Adaptive LMS Delay Measurement in dual Blood Volume Pulse Signals for Non-Invasive Monitoring," *IEEE*, pp. 117-120 (1997).

Crilly, Paul B., et al.; "An Integrated Pulse Oximeter System for Telemedicine Applications," *IEEE Instrumentation and Measurement Technology Conference*, Ottawa, Canada; May 19-21, 1997; pp. 102-104.

DeKock, Marc; "Pulse Oximetry Probe Adhesive Disks: a Potential for Infant Aspiration," *Anesthesiology*, vol. 89, pp. 1603-1604 (1998).

East, Christine E., et al.; "Fetal Oxygen Saturation and Uterine Contractions During Labor," *American Journal of Perinatology*, vol. 15, No. 6, pp. 345-349 (Jun. 1998).

Rhee, Sokwoo, et al.; "The Ring Sensor: a New Ambulatory Wearable Sensor for Twenty-Four Hour Patient Monitoring," *Proceedings of the 20th annual International Conference of the IEEE Engineering in Medicine and Biology Society*, vol. 20, No. 4, pp. 1906-1909 (Oct. 1998).

Yang, Boo-Ho, et al.; "A Twenty-Four Hour Tele-Nursing System Using a Ring Sensor," *Proceedings of the 1998 IEEE International Conference on Robotics & Automation*, Leaven, Belgium, May 1998; pp. 387-392.

König, Volker, et al.; "Reflectance Pulse Oximetry—Principles and Obstetric Application in the Zurich System," *Journal of Clinical Monitoring and Computing*, vol. 14, pp. 403-412 (1998).

Nogawa, Masamichi, et al.; "A Novel Hybrid Reflectance Pulse Oximater Sensor with improved Linearity and General Applicability to Various Portions of the Body," *Proceedings of the 20th Annual International Conference of the IEEE Engineering in Medicine and Biology Society*, vol. 20, No. 4, pp. 1858-1861 (1998).

Hayes, Matthew J., et al.; "Quantitative evaluation of photoplethysmographic artifact reduction for pulse oximetry," *SPIE*, vol. 3570, pp. 138-147 (Sep. 1998).

Edrich, Thomas, et al.; "Can the Blood Content of the Tissues be Determined Optically During Pulse Oximetry Without Knowledge of the Oxygen Saturation?—An In-Vitro Investigation," *Proceedings of the 20th Annual International conference of the IEEE Engineering in Medicine and Biology Society*, vol. 20, No. 6, pp. 3072-3075 (1998).

Hayes, Matthew J., et al.; "Artifact reduction in photoplethysmography," *Applied Optics*, vol. 37, No. 31, pp. 7437-7446 (Nov. 1998).

Such, Hans Olaf; "Optoelectronic Non-invasive Vascular Diagnostics Using multiple Wavelength and Imaging Approach," *Dissertation*, (1998).

Lutter, N., et al.; "Comparison of Different Evaluation Methods for a Multi-wavelength Pulse Oximeter," *Biomedizinische Technik*, vol. 43, (1998).

Ferrell, T.L., et al.; "Medical Telesensors," *SPIE*, vol. 3253, pp. 193-198 (1998).

Todd, Bryan, et al.; "The Identification of Peaks in Physiological Signals," *Computers and Biomedical Research*, vol. 32, pp. 322-335 (1999).

Rhee, Sokwoo, et al.; "Design of a Artifact-Free Wearable Plethysmographic Sensor," *Proceedings of the First joint BMES/EMBS Conference*, Oct. 13-16, 1999, Altanta, Georgia, p. 786.

Rohling, Roman, et al.; "Clinical Investigation of a New Combined Pulse Oximetry and Carbon Dioxide Tension Sensor in Adult Anaesthesia," *Journal o Clinical Monitoring and Computing*, vol. 15; pp. 23-27 (1999).

Ikeda, Kenji, et al.; "Improvement of Photo-Electric Plethysmograph Applying Newly Developed Opto-Electronic Devices," *IEEE Tencon*, pp. 1109-1112 (1999).

Kaestle, S.; "An Algorithm for Reliable Processing of Pulse Oximetry Signals Under strong Noise Conditions," *Dissertation Book*, Lubeck University, Germany (1999).

Seelbach-Göbel, Birgit, et al.; "The prediction of fetal acidosis by means of intrapartum fetal pulse oximetry," *Am J. Obstet. Gynecol.*, vol. 180, No. 1, Part 1, pp. 73-81 (1999).

Yang, Boo-Ho, et al.; "Development of the ring sensor for healthcare automation," *Robotics and Autonomous Systems*, vol. 30, pp. 273-281 (2000).

Rhee, Sokwoo, et al.; "Artifact-Resistant, Power-Efficient Design of Finger-Ring Plethysmographic Sensor—Part I: Design and Analysis," *Proceedings of the 22$^{nd}$ Annual EMBS International Conference*, Chicago, Illinois; Jul. 23-28, 2000; pp. 2792-2795.

Rhee, Sokwoo, et al.; "Artifact-Resistant, Power-Efficient Design of Finger-Ring Plethysmographic Sensor—Part II: Prototyping and Benchmarking," *Proceedings of the 22$^{nd}$ Annual EMBS International Conference*, Chicago, Illinois; Jul. 23-28, 2000; pp. 2796-2799.

Vicenzi, Martin N.; "Transesophageal versus surface pulse oximetry in intensive care unit patients," *Crit. Care Med.*; vol. 28, No. 7, pp. 2268-2270 (2000).

Goldman, Julian M.; "Masimo Signal Extraction Pulse Oximetry," *Journal of Clinical Monitoring and Computing*, vol. 16, pp. 475-483 (2000).

Coetzee, Frans M.; "Noise-Resistant Pulse Oximetry Using a Synthetic Reference Signal," *IEEE Transactions on Biomedical Engineering*, vol. 47, No. 8, Aug. 2000, pp. 1018-1026.

Nilsson, Lena, et al.; "Monitoring of Respiratory Rate in Postoperative Care Using a New Photoplethysmographic Technique," *Journal of Clinical Monitoring and Computing*, vol. 16, pp. 309-315 (2000).

Nijland, Mark J.M., et al.; "Assessment of fetal scalp oxygen saturation determination in the sheep by transmission pulse oximetry," *Am. J. Obstet Gynecol.*, vol. 183, No. 6, pp. 1549-1553 (Dec. 2000).

Edrich, Thomas, et al.; "Pulse Oximetry: An Improved In Vitro Model that Reduces Blood Flow-Related Artifacts," *IEEE Transactions on Biomedical Engineering*, vol. 47, No. 3, pp. 338-343 (Mar. 2000).

Schulz, Christian Eric; "Design of a Pulse Oximetry Sensor Housing Assembly," California State University Master's Thesis, *UMI Dissertation Services*, UMI No. 1401306, (May 2000) 63 pages.

Yao, Jianchu, et al.; "Design of a Plug-and-Play Pulse Oximeter," *Proceedings of the Second Joint EMBS/BMES Conference*, Houston, Texas, Oct. 23-26, 2002; pp. 1752-1753.

Aoyagi, T., et al.; "Pulse Oximeters: background, present and future," *Neonatal Care*, vol. 13, No. 7, pp. 21-27 (2000) (Article in Japanese—contains English summary of article).

Yokota, Nakaura, Takahashi, et al.; "Pilot Model of a Reflectance-Type Pulse Oximeter for Pre-hospital Evaluation," *Journal of the Japanese Society of Emergency Medicine*, Kanto Region, vol. 21, pp. 26-27 (2000) (Article in Japanese—contains English summary of article).

Kaestle, S.; "Determining Artefact Sensitivity of New Pulse Oximeters in Laboratory Using Signals Obtained from Patient," *Biomedizinische Technik*, vol. 45 (2000).

Cubeddu, Rinaldo, et al.; "Portable 8-channel time-resolved optical imager for functional studies of biological tissues," *Photon Migration, Optical Coherence Tomography, and Microscopy, Proceedings of SPIE*, vol. 4431, pp. 260-265 (2001).

Gisiger, P.A., et al.; "OxiCarbo®, a single sensor for the non-invasive measurement of arterial oxygen saturation and $CO_2$ partial pressure at the ear lobe," *Sensor and Actuators*, vol. B-76, pp. 527-530 (2001).

Cysewska-Sobusaik, Anna; "Metrological Problems With noninvasive Transillumination of Living Tissues," *Proceedings of SPIE*, vol. 4515, pp. 15-24 (2001).

Rhee, Sokwoo, et al.; "Artifact-Resistant, Power-Efficient Design of Finger-Ring Plethysmographic Sensor," *IEEE Transactions on Biomedical Engineering*, vol. 48, No. 7, pp. 795-805 (Jul. 2001).

Belal, Suliman Yousef, et al.; "A fuzzy system for detecting distorted plethysmogram pulses in neonates and paediatric patients," *Physiol. Meas.*, vol. 22, pp. 397-412 (2001).

Hayes, Matthew J., et al.; "A New Method for Pulse Oximetry Possessing Inherent Insensitivity to Artifact," *IEEE Transactions on Biomedical Engineering*, vol. 48, No. 4, pp. 452-461 (Apr. 2001).

Gosney, S., et al.; "An alternative position for the pulse oximeter probe," *Anaesthesia*, vol. 56, p. 493 (2001).

Silva, Sonnia Maria Lopez, et al.; "NIR transmittance pulse oximetry system with laser diodes," *Clinical Diagnostic Systems, Proceedings of SPIE*, vol. 4255, pp. 80-87 (2001).

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Earthrowl-Gould, T., et al.; "Chest and abdominal surface motion measurement for continuous monitoring of respiratory function," *Proc. Instn Mech Engrs*, V215, Part H; pp. 515-520 (2001).

Gehring, Harmut, et al.; "The Effects of Motion Artifact and Low Perfusion on the Performance of a New Generation of Pulse Oximeters in Volunteers Undergoing Hypoxemia," *Respiratory Care*, Vo. 47, No. 1, pp. 48-60 (Jan. 2002).

Jopling, Michae W., et al.; "Issues in the Laboratory Evaluation of Pulse Oximeter Performance," *Anesth Analg*, vol. 94, pp. S62-S68 (2002).

Gostt, R., et al.; "Pulse Oximetry Artifact Recognition Algorithm for Computerized Anaesthetic Records," *Journal of Clinical Monitoring and Computing Abstracts*, p. 471 (2002).

Chan, K.W., et al.; "17.3: Adaptive Reduction of Motion Artifact from Photoplethysmographic Recordings using a Variable Step-Size LMS Filter," *IEEE*, pp. 1343-1346 (2002).

Relente, A.R., et al.; "Characterization and Adaptive Filtering of Motion Artifacts in Pulse Oximetry using Accelerometers," *Proceedings of the Second joint EMBS/BMES Conference*, Houston, Texas, Oct. 23-26, 2002; pp. 1769-1770.

Yamaya, Yoshiki, et al.; "Validity of pulse oximetry during maximal exercise in normoxia, hypoxia, and hyperoxia," *J. Appl. Physiol.*, vol. 92, pp. 162-168 (2002).

Lutter, Norbert O., et al.; "False Alarm Rates of Three Third-Generation Pulse Oximeters in PACU, ICU and IABP Patients," *Anesth Analg*, vol. 94, pp. S69-S75 (2002).

Lutter, N., et al.; "Accuracy of Noninvasive Continuous Blood Pressure; Measurement Utilising the Pulse Transit Time," *Journal of clinical Monitoring and Computing*, vol. 17, Nos. 7-8, pp. 469 (2002).

Liu, Ying, et al.; "Sensor design of new type reflectance pulse oximetry," *Optics in Health Care and Biomedical Optics: Diagnostics and Treatment, Proceedings of SPIE*, vol. 4916, pp. 98-102 (2002).

Kyriacou, Panayiotis A., et al.; "Esophageal Pulse Oximetry Utilizing Reflectance Photoplethysmography," *IEEE Transactions on Biomedical Engineering*, vol. 49, No. 11, pp. 1360-1368 (Nov. 2002).

Kyriacou, P. A., et al.; "Investication of oesophageal photoplethysmographic signals and blood oxygen saturation measurements in cardiothoracic surgery patients," *Physiological Measurement*, vol. 23, No. 3, pp. 533-545 (Aug. 2002).

Tobata, H., et al.; "Study of Ambient Light Affecting Pulse Oximeter Probes," *Ikigaku* (*Medical Technology*), vol. 71, No. 10, pp. 475-476 (2002) (Article in Japanese—contains English summary of article).

Irie, A., et al.; "Respiration Monitors—Pulse Oximeters," *Neonatal Care*, vol. 15, No. 12, pp. 78-83 (2002) (Article in Japanese—contains English summary of article).

Koga, I., et al.; "Sigmoid colonic reflectance pulse oximetry and tonometry in a porcine experimental hypoperfusion shock model," *Acta Anaesthesiol Scand*, vol. 46, pp. 1212-1216 (2002).

Shaltis, Phillip, et al.; "Implementation and Validation of a Power-Efficient, High-Speed Modulation Design for Wireless Oxygen Saturation Measurement Systems," *IEEE*, pp. 193-194 (2002).

Warren, Steve, et al.; "Wearable Sensors and Component-Based Design for Home Health Care," *Proceedings of the Second Joint EMBS/BMES Conference*, Houston, Texas; Oct. 23-26, 2002; pp. 1871-1872.

Ericson, M.N., et al.; "In vivo application of a minimally invasive oximetry based perfusion sensor," *Proceedings of the Second Joint EMBS/BMES Conference*, Houston, Texas; Oct. 23-26, 2002, pp. 1789-1790.

Yoon, Gilwon, et al.; Multiple diagnosis based on Photoplethysmography: hematocrib, SpO2, pulse and respiration, *Optics in Health Care and Biomedical optics: Diagnostics and Treatment; Proceedings of the SPIE*, vol. 4916; pp. 185-188 (2002).

Hase, Kentaro, et al.; "Continuous Measurement of Blood Oxygen Pressure Using a Fiber Optic Sensor Based on Phosphorescense Quenching," *Proceedings of the Second Joint EMBS/BMES Conference*, Houston, Texas; Oct. 23-26, 2002, pp. 1777-1778.

Pothisarn, W., et al.; "A non-invasive hemoglobin measurement based pulse oximetry," *Optics in Health Care and Biomedical Optics: Diagnostics and Treatment; Proceedings of SPIE*, vol. 4916; pp. 498-504 (2002).

Tremper, K.K.; "A Second Generation Technique for Evaluating Accuracy and Reliability of Second Generation Pulse Oximeters," *Journal of Clinical Monitoring and Computing*, vol. 16, pp. 473-474 (2002).

Silva, Sonnia Maria Lopez, et al.; "Near-infrared transmittance pulse oximetry with laser diodes," *Journal of Biomedical Optics*, vol. 8, No. 3, pp. 525-533 (Jul. 2003).

Cyrill, D., et al.; "Adaptive Comb Filter for Quasi-Periodic Physiologic Signals," *Proceedings of the 25th Annual International Conference of the IEEE EMBS*, Cancun, Mexico, Sep. 17-21, 2003; pp. 2439-2442.

Matthews, Nora S. et al.; "An evaluation of pulse oximeters in dogs, cats and horses," *Veterinary Anaesthesia and Analgesia*, vol. 30, pp. 3-14 (2003).

Stetson, Paul F.; "Determining Heart Rate from Noisey Pulse Oximeter Signals Using Fuzzy Logic," *The IEEE International Conference on Fuzzy Systems*, St. Louis, Missouri, May 25-28, 2003; pp. 1053-1058.

Aoyagi, Takuo; "Pulse oximetry: its invention, theory, and future," *Journal of Anesthesia*, vol. 17, pp. 259-266 (2003).

Avidan, A.; "Pulse oximeter ear probe," *Anaesthesia*, vol. 58, pp. 726 (2003).

Lee, C.M., et al.; "Reduction of motion artifacts from photoplethysmographic recordings using wavelet denoising approach," *IEEE EMBS Asian-Pacific Conference on Biomedical Engineering*, Oct. 20-22, 2003; pp. 194-195.

Mendelson, Y., et al.; "Measurement Site and Photodetector Size Considerations in Optimizing Power Consumption of a Wearable Reflectance Pulse Oximeter," *Proceedings of the 25th Annual International conference of the IEEE EMBS*, Cancun, Mexico, Sep. 17-21, 2003; pp. 3016-3019.

Itoh, K., et al.; "Pulse Oximeter," *Toyaku Zasshi* (Toyaku Journal), vol. 25, No. 8, pp. 50-54 (2003) (Article in Japanese—contains English summary of article).

Matsui, A., et al.; "Pulse Oximeter," *Neonatal Care*, vol. 16, No. 3, pp. 38-45 (2003) (Article in Japanese—contains English summary of article).

Nakagawa, M., et al.; "Oxygen Saturation Monitor," *Neonatal Monitoring*, vol. 26, No. 5, pp. 536-539 (2003) (Article in Japanese—contains English summary of article).

Kubota, H., et al.; "Simultaneous Monitoring of PtcCO2 and SpO2 using a Miniature earlobe sensor," *Jinko Kokyo* (*Aritifficial Respiration*), vol. 20, No. 1, pp. 24-29 (2003).

Lebak, J.W., et al.; "Implementation of a Standards-Based Pulse Oximeter on a Wearable, Embedded Platform," *Proceeding of the 25th Annual International Conference of the IEEE EMBS*, Cancun, Mexico, Sep. 17-21, 2003; pp. 3196-3198.

Nagl, L., et al.; "Wearable Sensor System for Wireless State-of-Health Determination in Cattle," *Proceeding of the 25th Annual International Conference of the IEEE EMBS*, Cancun, Mexico, Sep. 17-21, 2003; pp. 3012-3015.

Östmark, Åke, et al.; "Mobile Medical Applications Made Feasible Through Use of EIS Platforms," *IMTC—Instrumentation and Measurement Technology Conference*, Vail, Colorado; May 20-22, 2003; pp. 292-295.

Warren, Steve, et al.; "A Distributed Infrastructure for Veterinary Telemedicine," *Proceedings of the 25th Annual International Conference of the IEEE EMBS*, Cancun, Mexico; Sep. 17-21, 2003; pp. 1394-1397.

Pujary, C., et al.; "Photodetector Size Considerations in the Design of a Noninvasive Reflectance Pulse Oximeter for Telemedicine Applications," *IEEE*, pp. 148-149 (2003).

A. Johansson; "Neural network for photoplethysmographic respiratory rate monitoring," *Medical & Biological Engineering & Computing*, vol. 41, pp. 242-248 (2003).

Reuss, James L.; "Factors Influencing Fetal Pulse Oximetry Performance," *Journal of clinical Monitoring and Computing*, vol. 18, pp. 13-14 (2004).

Mannheimer, Paul D., et al.; "The influence of Larger Subcutaneous Blood Vessels on Pulse Oximetry," *Journal of clinical Monitoring and Computing*, vol. 18, pp. 179-188 (2004).

Wendelken, Suzanne, et al.; "The Feasibility of Using a Forehead Reflectance Pulse Oximeter for Automated Remote Triage," *IEEE*, pp. 180-181 (2004).

Lopez-Silva, S.M., et al.; "Transmittance Photoplethysmography and Pulse Oximetry With Near Infrared Laser Diodes," *IMTC 2004—Instrumentation and Measurement Technology Conference*, Como, Italy, May 18-20, 2004; pp. 718-723.

Sugino, Shigekzau, et al.; "Forehead is as sensitive as finger pulse oximetry during general anesthesia," *Can J. Anesth.; General Anesthesia*, vol. 51, No. 5; pp. 432-436 (2004).

Addison, Paul S., et al.; "A novel time-frequency-based 3D Lissajous figure method and its application to the determination of oxygen saturation from the photoplethysmogram," *Institute of Physic Publishing, Meas. Sci. Technol.*, vol. 15, pp. L15-L18 (2004).

Jovanov, E., et al.; "Reconfigurable intelligent Sensors for Health Monitoring: A case Study of Pulse Oximeter Sensor," *Proceedings o the 26th Annual International conference of the IEEE EMBS*, San Francisco, California, Sep. 1-5, 2004, pp. 4759-4762.

Kocher, Serge, et al.; "Performance of a Digital PCO$_2$/SPO$_2$ Ear Sensor," *Journal of Clinical Monitoring and Computing*, vol. 18, pp. 75-59 (2004).

Yao, Jianchu, et al.; "A Novel Algorithm to Separate Motion Artifacts from Photoplethysmographic Signals Obtained With a Reflectance Pulse Oximeter," *Proceedings of the 26th Annual International conference of the IEEE EMBS*, San Francisco, California, Sep. 1-5, 2004; pp. 2153-2156.

Nuhr, M., et al.: "Forehead SpO$_2$ monitoring compared to finger SpO$_2$ recording in emergency transport," *Anaesthesia*, vol. 59, pp. 390-393 (2004).

Johnston, William S , et al.; "Effects of Motion Artifacts on helmet-Mounted Pulse Oximeter Sensors," 2 pgs. (2004).

Branche, Paul C., et al.; "Measurement Reproducibility and Sensor Placement Considerations in Designing a Wearable Pulse Oximeter for Military Applications," 2 pgs. (2004).

Kocher, Serge, et al.; "Performance of a Digital PCO$_2$/SPO$_2$ Ear Sensor," *Journal of Clinical Monitoring and Computing*, vol. 18, pp. 75-79 (2004).

Heuss, Ludwig T., et al.; "Combined Pulse Oximetry / Cutaneous Carbon dioxide Tension Monitoring During Colonoscopies: Pilot study with a Smart Ear Clip," *Digestion*, vol. 70, pp. 152-158 (2004).

Matsuzawa, Y., et al.; "Pulse Oximeter," *Home Care Medicine*, pp. 42-45 (Jul. 2004); (Article in Japanese—contains English summary of article).

Crespi, F., et al.; "Near infrared oxymeter prototype for non-invasive analysis of rat brain oxygenation," *Optical Sensing, Proceedings of SPIE*, vol. 5459, pp. 38-45 (2004).

Johnston, W.S., et al.; "Extracting Breathing Rate Infromation from a Wearable Reflectance Pulse Oximeter Sensor," *Proceedings of the 26th Annual International conference of the IEEE EMBS*, San Francisco, California; Sep. 1-5, 2004; pp. 5388-5391.

Spigulis, Janis, et al.; "Optical multi-channel sensing of skin blood pulsations," *Optical Sensing, Proceedings of SPIE*, vol. 5459, pp. 46-53 (2004).

Yan, Yong-sheng, et al.; "Reduction of motion artifact in pulse oximetry by smoothed pseudo Wigner-Ville distribution," *Journal of NeuroEngineering and Rehabilitation*, vol. 2, No. 3 (9 pages) (Mar. 2005).

Urquhart, C., et al.; "Ear probe pulse oximeters and neonates," *Anaesthesia*, vol. 60, p. 294 (2005).

J. Hayoz, et al.; "World's First Combined digital Pulse Oximetry Pulse Oximetry and Carbon Dioxide Tension Ear Sensor", *Abstracts*, A6, p. S103. (undated).

J. Huang, et al.; "Low Power Motion Tolerant Pulse Oximetry," *Abstracts*, A7, p. S103. (undated).

P. Lang, et al.; "Signal Identification and Quality Indicator™ for Motion Resistant Pulse Oximetry," *Abstracts*, A10, p. S105. (undated).

Hamilton, Patrick S., et al.; "Effect of Adaptive Motion-Artifact Reduction on QRS Detection," *Biomedical Instrumentation & Technology*, pp. 197-202 (undated).

Kim, J.M., et al.; "Signal Processing Using Fourier & Wavelet Transform," pp. II-310-II-311 (undated).

Lee, C.M., et al.; "Reduction of Motion Artifacts from Photoplethysmographic Records Using a Wavelet Denoising Approach," *IEEE*, pp. 194-195 (undated).

Nogawa, Masamichi, et al.; "A New Hybrid Reflectance Optical Pulse Oximetry Sensor for Lower Oxygen Saturation Measurement and for Broader Clinical Application," *SPIE*, vol. 2976, pp. 78-87 (undated).

Odagiri, Y.; "Pulse Wave Measuring Device," *Micromechatronics*, vol. 42, No. 3, pp. 6-11 (undated) (Article in Japanese—contains English summary of article).

Yamazaki, Nakaji, et al.; "Motion Artifact Resistant Pulse Oximeter (Durapulse PA 2100)," *Journal of Oral Cavity Medicine*, vol. 69, No. 4, pp. 53 (date unknown) (Article in Japanese—contains English summary of article).

MEDICAL SENSOR AND TECHNIQUE FOR USING THE SAME

CROSS-REFERENCE TO RELATED APPLICATIONS

This application is a continuation of U.S. application Ser. No. 11/240,682, filed Sep. 30, 2005, the disclosure of which is hereby incorporated by reference in its entirety for all purposes.

BACKGROUND OF THE INVENTION

1. Field of the Invention

The present invention relates generally to medical devices and, more particularly, to sensors used for sensing physiological parameters of a patient.

2. Description of the Related Art

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring many such physiological characteristics. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin in arterial blood, the volume of individual blood pulsations supplying the tissue, and/or the rate of blood pulsations corresponding to each heartbeat of a patient. In fact, the "pulse" in pulse oximetry refers to the time varying amount of arterial blood in the tissue during each cardiac cycle.

Pulse oximeters typically utilize a non-invasive sensor that transmits light through a patient's tissue and that photoelectrically detects the absorption and/or scattering of the transmitted light in such tissue. One or more of the above physiological characteristics may then be calculated based upon the amount of light absorbed or scattered. More specifically, the light passed through the tissue is typically selected to be of one or more wavelengths that may be absorbed or scattered by the blood in an amount correlative to the amount of the blood constituent present in the blood. The amount of light absorbed and/or scattered may then be used to estimate the amount of blood constituent in the tissue using various algorithms.

Pulse oximetry readings depend on pulsation of blood through the tissue. Thus, any event that interferes with the ability of the sensor to detect that pulsation can cause variability in these measurements. Motion artifacts occur when a patient's movements cause interference in the signal detected by the sensor. Motion artifacts can also occur in response to forces acting on the sensor. For example, a patient may be jostled by healthcare workers in emergency room settings. The type location, amount, or duration of force acting on a sensor will determine the nature of the motion artifact.

Generally, sensors are vulnerable to motion artifacts when the optical distance, or path length, orientation, or angle between a sensor's emitter and detector varies due to an undesired mechanical change in the conformation of the sensor while in use. The mechanical deformation of the sensor may be in the form of a compression of the sensor, causing a decrease in path length. Alternately, a sensor may flex or move in a manner that increases the distance between an emitter and detector, resulting in an increase in path length. In any case, variability in the optical path length due to motion can cause motion artifacts and obscure the desired pulse oximetry signal.

SUMMARY

Certain aspects commensurate in scope with the originally claimed invention are set forth below. It should be understood that these aspects are presented merely to provide the reader with a brief summary of certain forms that the invention might take and that these aspects are not intended to limit the scope of the invention. Indeed, the invention may encompass a variety of aspects that may not be set forth below.

There is provided a sensor that includes: a sensor body; at least one sensing element disposed on the sensor body; and a pressure-sensitive structure associated with the sensor body, wherein the pressure-sensitive structure is adapted to provide a feedback related to a pressure applied to the sensor body.

There is also provided a pulse oximetry system that includes a pulse oximetry monitor and a pulse oximetry sensor adapted to be operatively coupled to the monitor. The sensor includes: a sensor body; at least one sensing element disposed on the sensor body; and a pressure-sensitive structure associated with the sensor body, wherein the pressure-sensitive structure is adapted to provide a feedback related to a pressure applied to the sensor body.

There is also provided a method of operating a sensor including: emitting light into a tissue with an emitter; detecting the light with a detector; measuring a physiological characteristic based on the detected light; detecting a force experienced by at least one of the emitter and the detector with a force-sensitive sensor; and triggering an alarm when the force is greater than a threshold value.

There is also provided a method of manufacturing a sensor that includes providing a sensor body on which at least one sensing element is disposed; and providing a pressure-sensitive structure disposed on the sensor body.

There is also provided a method that includes: acquiring pressure data and oxygen saturation data from a sensor; correlating the acquired pressure data to a set of reference artifact data; and determining if the oxygen saturation data comprises a motion artifact.

BRIEF DESCRIPTION OF THE DRAWINGS

Advantages of the invention may become apparent upon reading the following detailed description and upon reference to the drawings in which.

DETAILED DESCRIPTION OF SPECIFIC EMBODIMENTS

Figure 1A:
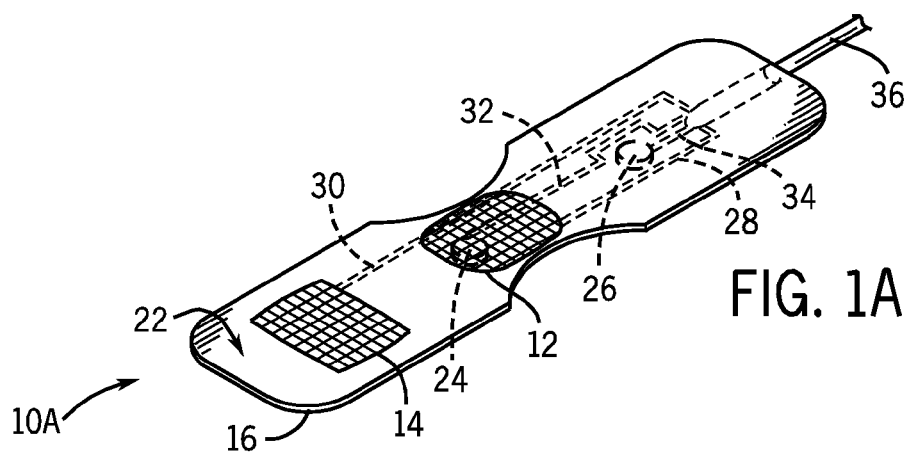
FIG. 1A illustrates a perspective view of an exemplary sensor featuring force-sensitive mesh regions.

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

In accordance with the present technique, sensors for pulse oximetry or other applications utilizing spectrophotometry are provided that reduce motion artifacts by correcting for the effects of patient movement and outside forces. For example, sensors are provided that include force-sensitive devices adapted to assess the pressure experienced by a sensor while in use. Further, sensors as provided herein may notify a user that above-normal pressures are being exerted on a sensor, which may prompt relocation of the sensor to a tissue site that is less subject to motion artifacts.

Motion artifacts in pulse oximetry are often generated by the movement of the sensor relative to the optically probed tissue, which is typically caused by patient movement or other forces acting on the sensor. Because pulse oximetry is often used in settings where it is difficult to prevent patient motion, it is desirable to provide a mechanism for reducing the effects of motion on the pulse oximetry measurement. For example, a squeezing motion by a patient may mechanically deform a sensor, causing the sensor's emitter and detector to temporarily change position relative to one another, resulting in a motion artifact. Similarly, outside forces, such as the mechanical force of an object pressing against a sensor, may also cause mechanical deformation of a sensor and movement of the sensing components.

It is desirable to account for the effect of forces on a sensor while in use by providing qualitative information indicating to a healthcare provider or other user that an event, such as a patient motion, is occurring that is likely to cause motion artifacts. In other embodiments, it is desirable to quantitatively assess the motion or force acting on a sensor in order to correct the sensor measurements accordingly. For example, a squeezing motion by a finger may be assessed by a sensor 10 as provided herein. The squeezing may mechanically deform a force-sensitive region on a sensor body applied to the finger. The force of squeezing may be converted to an electrical signal that is sent to a monitor in order to assess the force experienced by the sensor and thus correct for the motion of the emitter relative to the detector.

Figure 1B:
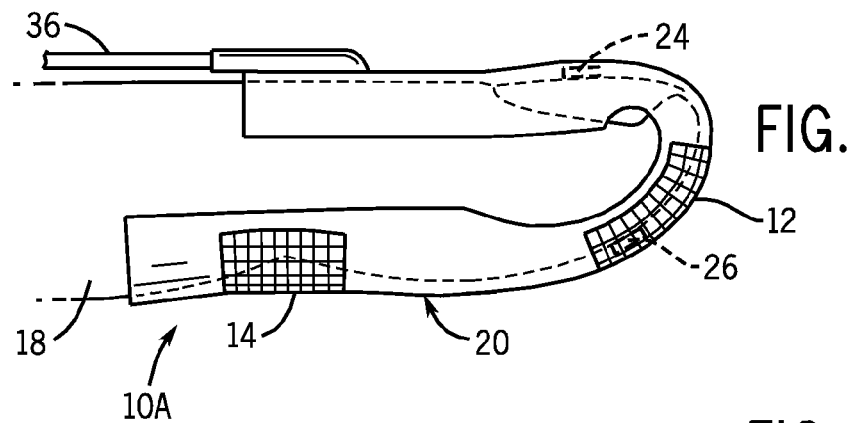
FIG. 1B illustrates a cross-sectional view of the sensor of FIG. 1A applied to a patient digit.
Figure 1C:
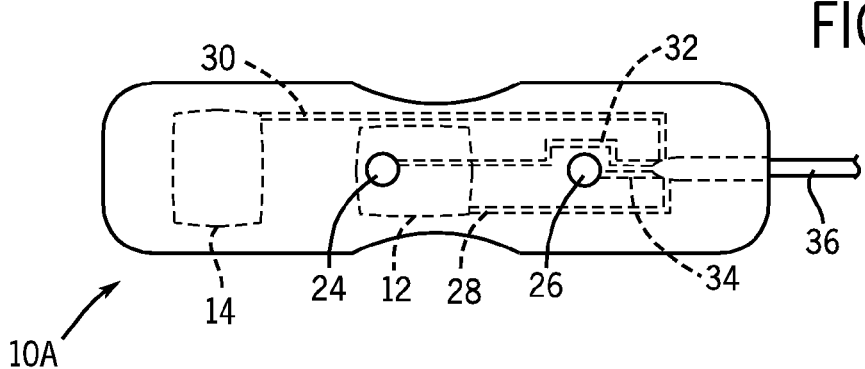
FIG. 1C illustrates a perspective view of the tissue-contacting surface of the sensor of FIG. 1A.

FIGS. 1A-C illustrate an exemplary bandage-style sensor 10A adapted for use on a digit. The sensor 10A has a force-sensitive structure 12 disposed on the sensor body 16 in a region corresponding to a fingertip region of a digit when the sensor 10A is applied to a digit 18, as shown in FIG. 1B. The sensor 10A, as depicted, also has a force-sensitive structure 14 disposed on the sensor body 16 in a region corresponding to a joint region of the digit 18. The force-sensitive sensors 12 and 14 may be disposed on the sensor body 16 on the surface 20 that does not contact the digit 18 during normal use. As shown in FIG. 1C, the force-sensitive sensors 12 and 14 may be disposed on the surface 20 of the sensor body 16 that opposes the tissue-contacting surface 22 upon which the emitter 24 and the detector 26 are disposed. In alternate embodiments, it is contemplated that the force-sensitive sensors 12 and 14 may be embedded in the sensor body 16 or disposed on the tissue-contacting surface 22.

The force-sensitive sensors 12 and 14 have input and output leads 28 and 30 respectively, which may be embedded in the sensor body 16. It is contemplated that the leads 28 and 30 may be connected to a cable 36 that also connects to the electrical lead 32 of the emitter 24 and the electrical lead 34 of the detector 26. As depicted, the force-sensitive sensors 12 and 14 may be flexible mesh-type arrays of multiple sensing elements, or may be flexible circuits.

In other embodiments, the sensor 10A may have additional force-sensitive sensors disposed on the sensor body 16. It may be advantageous to provide force-sensitive sensors on multiple sides of the sensor 10A, as it is difficult to predict the types of motion that the sensor 10A may experience. For example, force-sensitive sensors may be distributed on the sensor body 16 in locations directly opposing each other across the digit 18. Such an arrangement may provide more complete information about a squeezing motion of the digit 18 at a joint, as a force-sensitive structure on the top of the digit 18 may experience a stretching force while a force-sensitive structure in the crease of the joint may experience a compression force. Further, force-sensitive sensors may be disposed on the sensor body 16 in regions that correspond to the sides of the digit to provide information about the pressure experienced by the sensor body 16 during a rolling motion of the digit 18.

Figure 2:
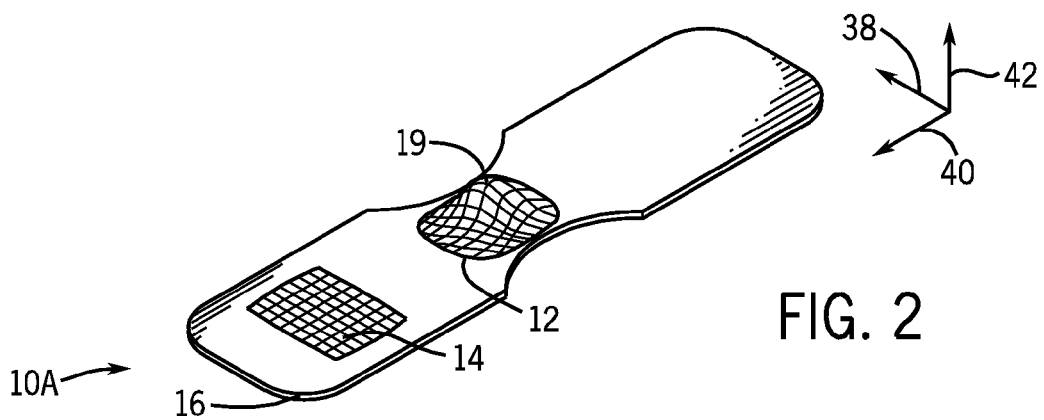
FIG. 2 illustrates a perspective view of the sensor of FIG. 1A after deformation of the force-sensitive mesh caused by finger tapping.

More specifically, FIG. 2 illustrates a perspective view of the sensor 10A with an exemplary deformation pattern of the force-sensitive structure 12 in response to a finger-tapping or pressing motion. An x-axis 38 and a y-axis 40 correspond to the plane of the sensor body 16. A z-axis 42 corresponds to the direction of pressure from the tapping motion of the digit 18. As the digit 18 presses against the tip of the sensor body 16, the force-sensitive structure 12 is deformed such that certain portions of the mesh form a peak-like structure 19. The deformation in response to pressure may cause certain intersection points in the grid of the force-sensitive structure 12 to be pushed closer together. As the distances between the intersection points change, the force-sensitive structure 12 may convert the change in the distances into an electrical signal that is related to the pressure experienced by the sensor 10A.

Figure 3:
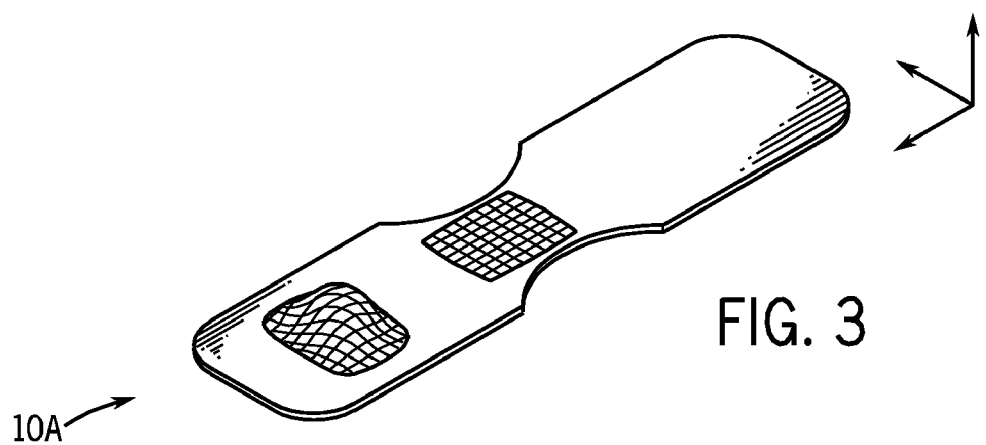
FIG. 3 illustrates a perspective view of the sensor of FIG. 1A after deformation of the force-sensitive mesh caused by finger squeezing at the joint.

Similarly, FIG. 3 illustrates a perspective view of the sensor 10A with an exemplary deformation pattern of the force-sensitive structure 14 in response to a finger squeezing motion. The z-axis 42 corresponds to the direction of pressure from a squeezing motion of the digit 18. As the digit 18 flexes at the joint, the force-sensitive structure 14 is deformed such that the mesh is compressed. The deformation in response to squeezing may cause certain intersection points in the grid of the force-sensitive structure 14 to be pushed closer together. As above, the change in the distance between intersection points of the grid of the force-sensitive structure may be converted into an electrical signal.

Figure 4A:
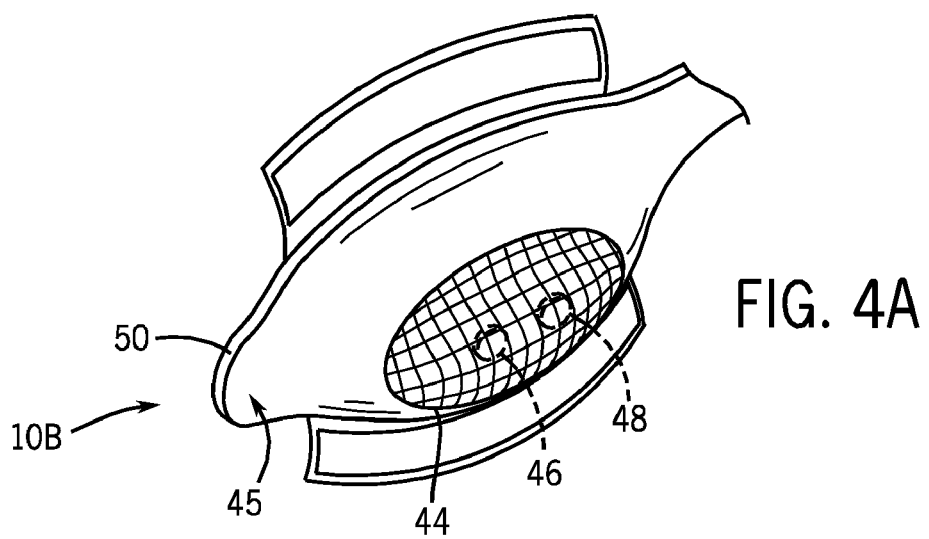
FIG. 4A illustrates a perspective view of an exemplary embodiment of a forehead sensor whereby the force-sensitive mesh is disposed in a region around the emitter and detector.
Figure 4B:
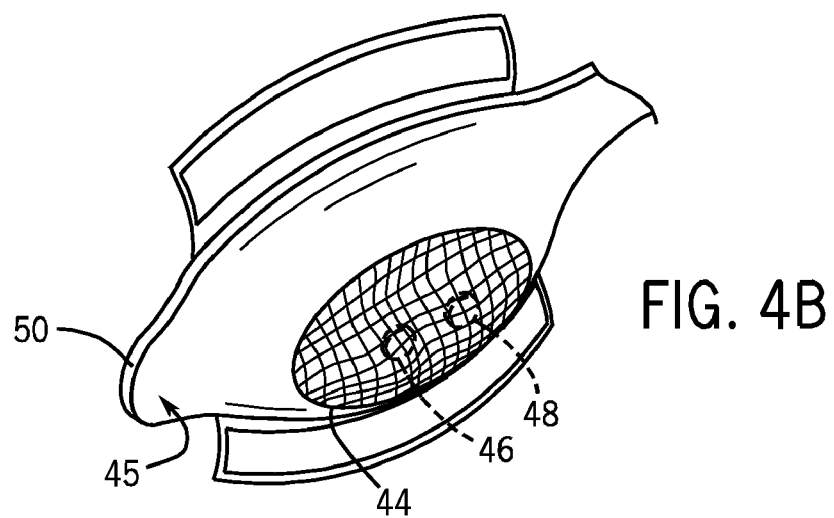
FIG. 4B illustrates a perspective view of the sensor of FIG. 4A after deformation of the force-sensitive mesh caused by pressing the sensor against an object.

It is also contemplated that a force-sensitive structure may be disposed on a sensor body in a region corresponding to at least one of an emitter or a detector. FIG. 4A illustrates a reflectance-type sensor 10B adapted for use on a patient's forehead. The sensor 10B has a force-sensitive structure 44 disposed on a tissue-contacting surface 45 of the sensor body 50. The emitter 46 and the detector 48 are surrounded by the force-sensitive structure 44, which deforms in response to outside forces, thereby providing a measure of the outside forces acting upon the emitter 46 and the detector 48. FIG. 4B illustrates an exemplary deformation of the force-sensitive structure 44 as it may appear after a patient has pressed the sensor 10B against a pillow or other object during normal wear.

Force-sensitive sensors as described herein may be any appropriate sensor that is capable of converting a force applied to a sensor body into an electrical signal. In certain embodiments, the pressure or force-sensitive structure may take the form of a displacement sensor. In one such embodiment, the pressure or force-sensitive structure may include a strain gauge or other mechanical displacement sensor. In another embodiment, the displacement sensor may include a linear variable differential transformer. In other embodiments, a force-sensitive structure may be a resistance-based sensor. Force-sensitive sensors, e.g. sensors 12, 14, and 44 may be disposed on the sensor body as electrodes, such as silver electrodes, printed as a matrix of intersecting rows and columns. An additional layer of semiconductive ink may provide an electrical resistance at each intersection on the matrix. Sandwiching these two layers together may create an array sensor. When a force is applied, the change in resistance is measured. Changing the formulation of the ink may produce different sensitivity ranges. Additionally, varying the spacing between rows and columns may yield finer resolution. In certain embodiments, a force-sensitive structure may have a spatial resolution, or sensor electrode spacing, of at least 0.0229 mm$^2$. An example of a resistance sensor that is appropriate for use with a sensor 10 according to the present techniques is Flexiforce® film or flexible circuits, available from Tekscan (South Boston, Mass.).

Pressure measurements may also be made by using polymers that are force-sensitive resistor materials. Force-sensitive resistor materials, such as those available from Interlink (Carptenteria, Calif.) and Advanced Composites Technology (Boston, Mass.) have a resistance variation under load. A force sensing resistor may be a piezoresistivity conductive polymer, which changes resistance in a predictable manner following application of force to its surface. It is normally supplied as a polymer sheet which has had the sensing film applied by screen printing. The sensing film typically includes both electrically conducting and non-conducting particles suspended in matrix. The particle sizes may be of the order of fraction of microns, and the particles may be formulated to reduce the temperature dependence, improve mechanical properties and increase surface durability. Applying a force to the surface of the sensing film causes particles to touch the conducting electrodes, changing the resistance of the film. Such a polymer-based force-sensitive resistor may be advantageous as it utilizes a relatively simple interface and can operate satisfactorily in moderately hostile environments.

In certain embodiments, the pressure or force-sensitive structure may take the form of a capacitance sensor. In such sensors, the capacitance is inversely proportional to the distance between the electrodes of the sensor. An exemplary capacitance-based sensor, TactArray, is available from Pressure Profile Systems (Los Angeles, Calif.). In certain embodiments, the capacitance sensor may be sensitive to forces or pressures from 1 psi to 200 psi.

Figure 5A:
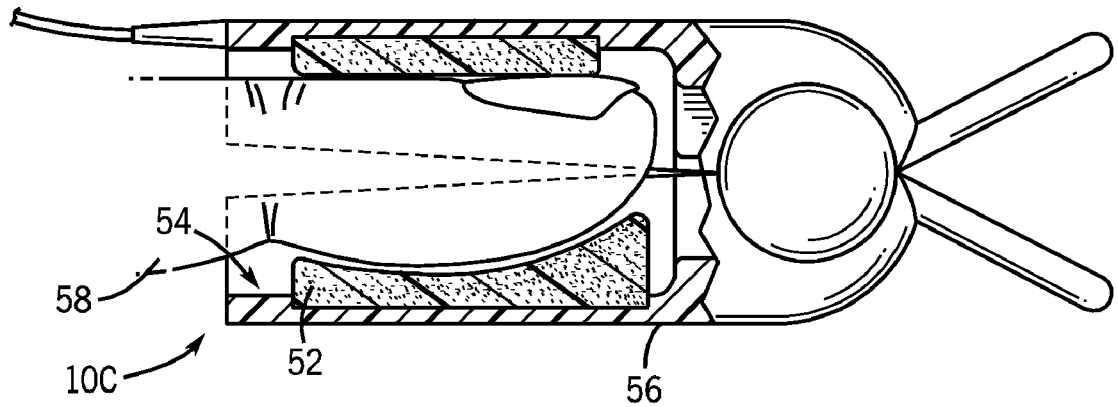
FIG. 5A illustrates a cross-sectional view of an exemplary embodiment of a clip-style sensor with force-sensitive foam disposed on the tissue-contacting side of the sensor.
Figure 5B:
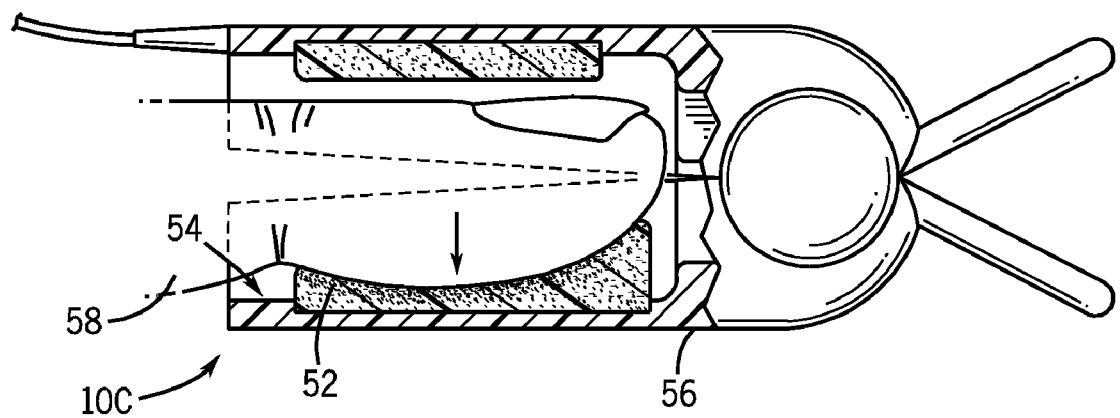
FIG. 5B illustrates a cross-sectional view of the pulse oximetry sensor of FIG. 5A in which the force-sensitive foam compresses in response to finger motion.

In a specific embodiment, it may be advantageous to provide a mechanism for monitoring movement of a digit within a relatively rigid clip-style sensor. FIGS. 5A-B illustrate a sensor 10C that includes an elastomeric foam that is sensitive to force. The force-sensitive foam 52 provides measurement of the resistance of a conductive elastomer or foam between two points. The force-sensitive foam may be a carbon doped rubber in which the resistance of the elastomer changes with the application of force, resulting from the deformation of the elastomer altering the particle density. As depicted, the force-sensitive foam is disposed on the tissue-contacting surface 54 of the sensor body 56. As the digit 58 moves within the sensor 10C, the foam is compressed, resulting in a change in the resistance of the foam. The electrical signal generated by the movement of the digit may be further processed to correct for any motion artifacts caused by the movement of the digit relative to the sensor 10C.

Figure 6A:
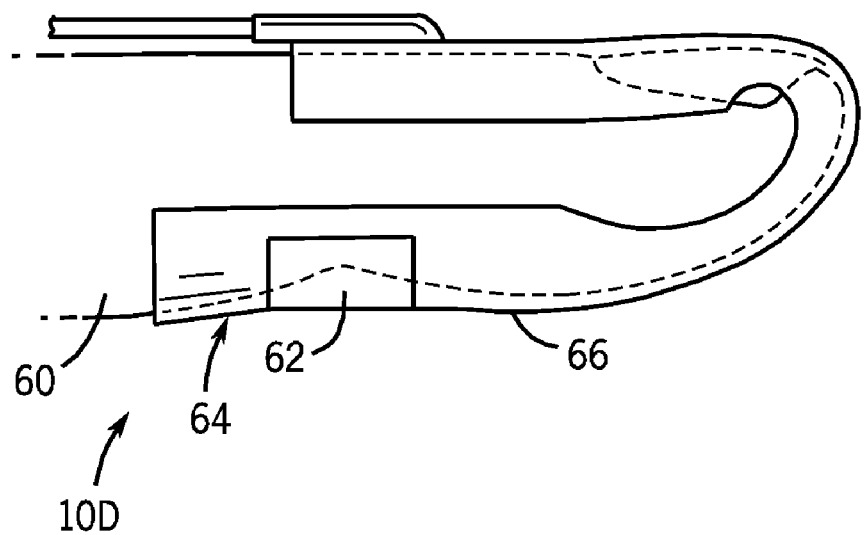
FIG. 6A illustrates a cross-sectional view of an exemplary embodiment of a sensor with a color-changing force-sensitive structure disposed on the sensor around the joint.
Figure 6B:
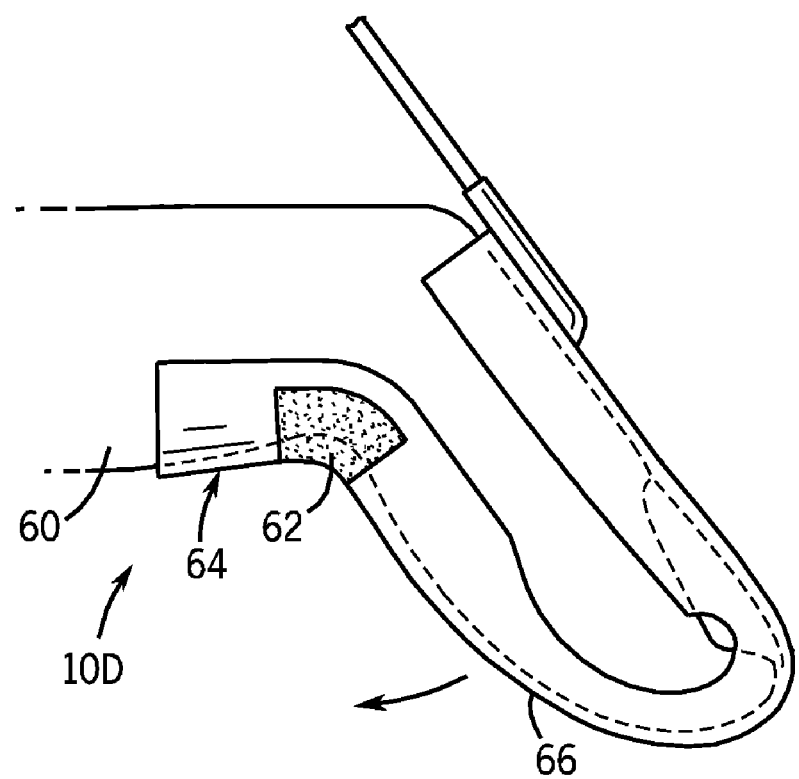
FIG. 6B illustrates a cross-sectional view of the pulse oximetry sensor of FIG. 6A in which flexing at the joint causes the force-sensitive structure to change from colorless to red.

In certain embodiments, it is envisioned that force or pressure data generated from the force-sensitive structures may be further processed to generate displays or other information related to a sensor 10 condition. However, as patients may not be familiar with the medical monitor icons and displays that may be used in conjunction with a sensor 10, in certain embodiments it may be advantageous to provide a sensor 10 with a force-sensitive signal that is easily identifiable by a patient. FIG. 6A illustrates a sensor 10D applied to a patient digit 60. The sensor 10D includes a force-sensitive structure 62 disposed on the surface 64 of the sensor body 66 that does not contact the digit during normal use. The force-sensitive structure 62 is adapted to change color upon the application of force. As illustrated in FIG. 6B, upon squeezing of the digit 60 at the first joint, the force-sensitive structure 62 changes color from colorless to red as pressure increased in the area of the force-sensitive structure 62. The force-sensitive structure 62 may be Pressurex® film, available from Sensor Products Inc. (East Hanover, N.J.), which increases in red color intensity in relation to the amount of force applied. A conscious patient may easily note the change in color and adjust his actions to prevent further movements that may be associated with motion artifacts and measurement errors.

Figure 7:
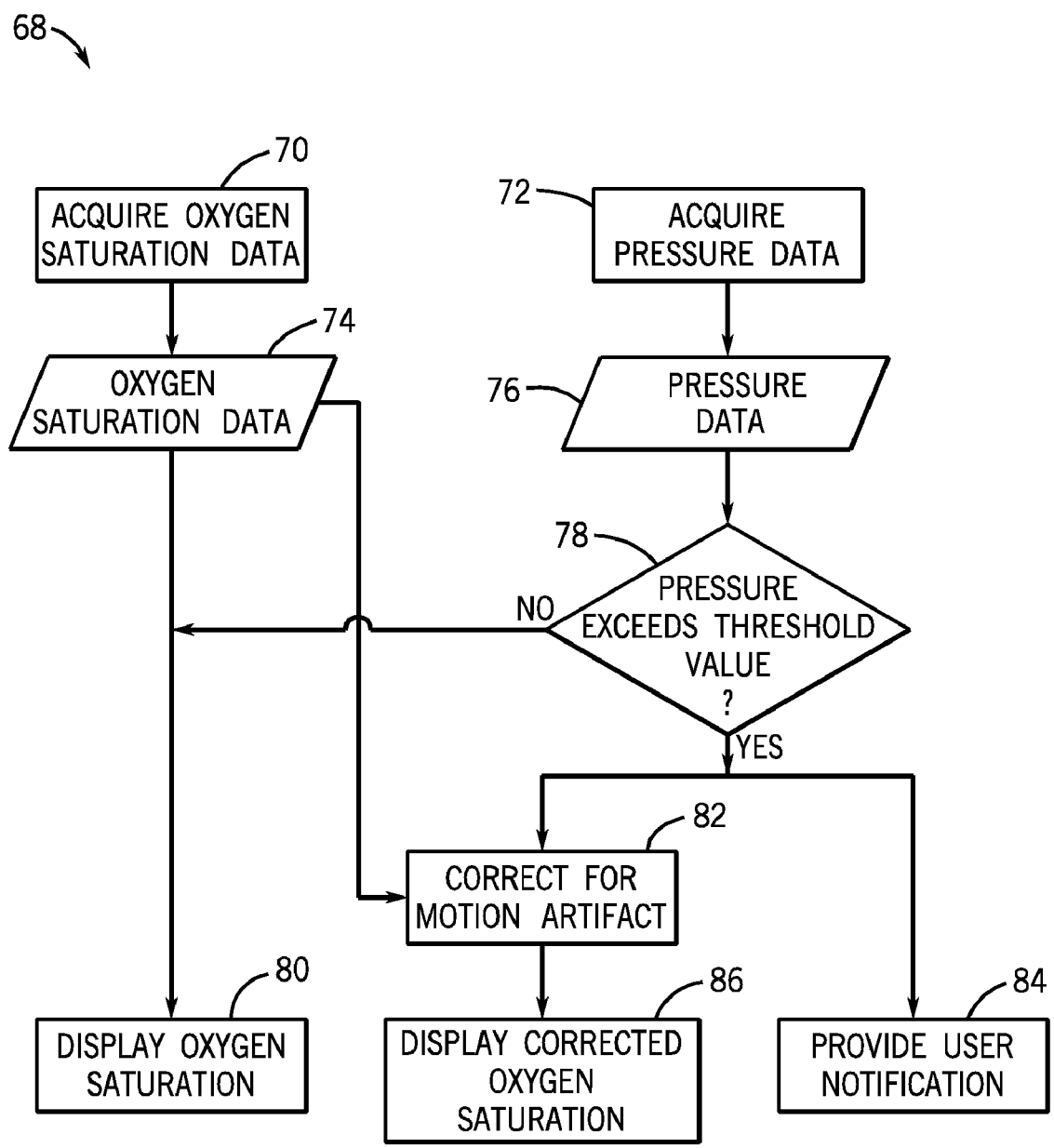
FIG. 7 is a flow chart of the alarm trigger responsive to sensor output according to the present invention.

It is envisioned that a sensor 10 as described herein may be used to provide information related to the pressure and forces experienced by the sensor 10 during use. Such information may be converted into an electrical signal and sent to a monitor or another appropriate device, as described in more detail below, for processing. The flow chart 68 depicted in FIG. 7 describes the downstream steps involved after step 70, which involves acquisition of the oxygen saturation data 74 from the sensor 10, and step 72, which involves acquisition of force or pressure data 76. In certain embodiments, it is envisioned that steps 70 and 72 may occur simultaneously.

At a step 78, a processor compares the pressure data 76 against a pressure threshold. Generally, the raw pressure data 76 output from a force-sensitive structure as described herein is further acted upon by a processor, such as a processor in a pulse oximeter, to provide either a pressure map or a pressure value. As a sensor 10 may provide separate pressure outputs from multiple force-sensitive structures, it may be advantageous to provide a map of the pressure variations at different locations on the sensor body. In other embodiments, it may be appropriate to provide a measure of the total pressure experienced by the sensor body, or the total pressure experienced at a single location, such as a fingertip location. The map or value may then be compared to a predetermined threshold map or predetermined threshold value. The threshold value is generally envisioned to be a pressure value that is associated with an increase in motion artifacts. A threshold map may be an image which may be directly compared to a pressure map obtained from the force-sensitive structure. If, at a step 78, the pressure data 76 does not exceed a predetermined threshold value, the processor passes control to step 80. At step 80, the system goes into a default mode and a processor calculates an oxygen saturation value from the oxygen saturation data 74. The oxygen saturation value may then be displayed on a monitor.

If, on the other hand, the pressure data 76 does exceed a threshold pressure value, the processor passes control to steps 82 and 84. In step 84, a notification is displayed to alert a user that the pressure experienced by a sensor 10 has increased beyond a critical threshold value. The notification may be an audio alarm, such as a warning sound, or a visual alarm, such as a text message or icon that is displayed on a monitor.

In step 82, a processor may act upon the oxygen saturation data 74 in order to correct for any influence of higher-than-normal pressures on the sensor 10. The corrected oxygen saturation value may then be displayed on the monitor. For example, a processor may adjust an estimation of the path length between an emitter and a detector to account for any reduction in the path length due to tissue compression. In such an example, measured pressure would be inversely related to path length. The adjustment of the path length may result in a correction in the oxygen saturation.

Figure 8:
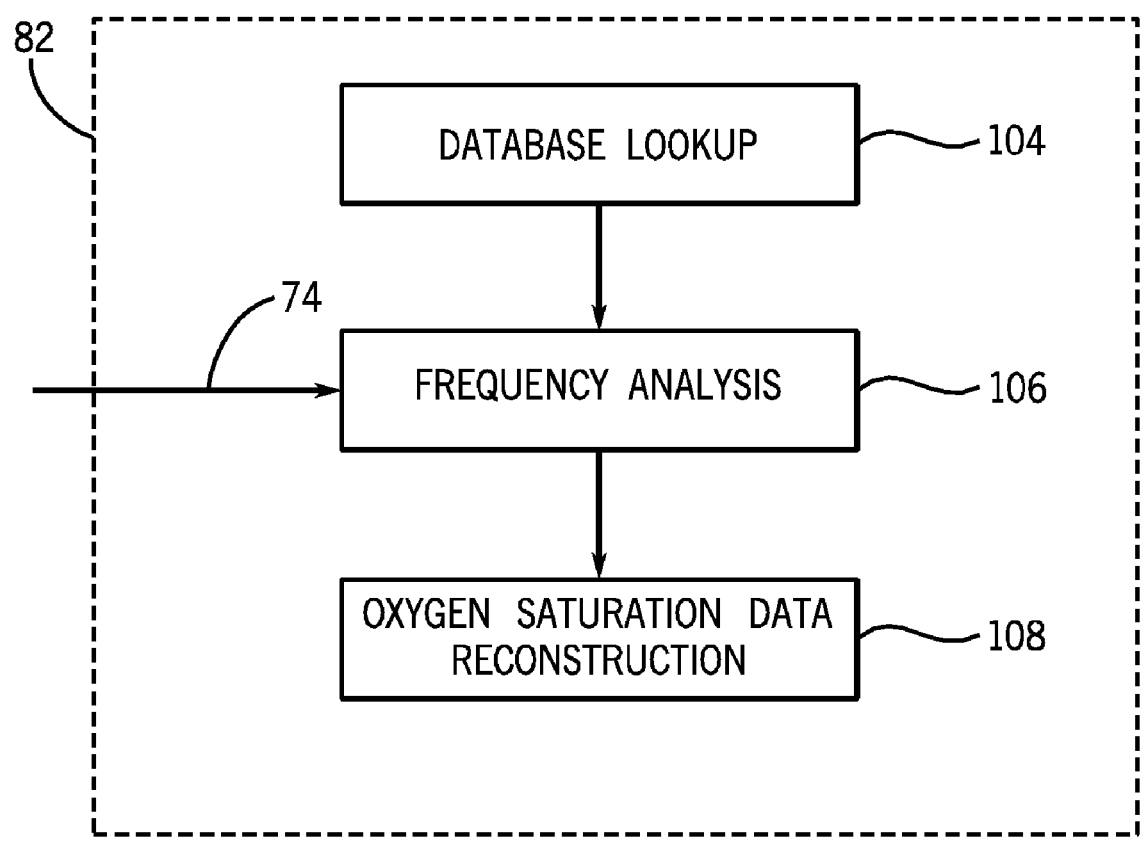
FIG. 8 is a more detailed flow chart of step 82 from FIG. 7.

In another embodiment, shown in FIG. 8, step 82 may be accomplished by correlating pressure data 76 to previously acquired or reference artifact data characteristic of different pressure events. At step 104, the pressure data 76 exceeding a pre-defined threshold at step 78 is provided as input into a searchable machine-readable database of artifact data to determine if the pressure data 76 is characteristic of particular artifact events. The look-up database of artifact in step 104 may be acquired through measurements of various pressure profiles associated with artifact events to build a look-up database or table that correlates pressure data 76 with possible artifact/interference-related saturation data. For example, the pressure data 76 may be compared to an artifact database in step 104 to determine if the pressure data 76 is characteristic of venous pooling under the fingertip during tapping or compartmentalization of blood in the finger during scratching. The oxygen saturation data 74 may then be corrected in light of the particular type of pressure experienced by the tissue. The database artifact/interference data obtained from step 104 that correlates with or is characteristic of the pressure data 76 is analyzed in frequency domain at step 106 using frequency transforms such as FFT (Fast Fourier Transform) and WT (Wavelet Transform). Additionally in step 106, frequency transforms are also applied to the acquired raw saturation data 74. At certain frequencies where found artifacts/interferences are located, the artifacts/interferences may be removed from saturation data in the frequency domain. The resultant corrected frequency domain saturation data (with artifact/interference removed) may then be used to reconstruct the clean time domain saturation signal via inverse transforms such as inverse FFT and inverse wavelet transform at step 108. The reconstructed oxygen saturation data may then be displayed in step 86.

In another embodiment (not shown), a sensor 10 may include a second emitter and detector pair located in a different position on the sensor body than the first emitter and detector pair. At step 78, a processor may note that pressure data 76 from the first emitter and detector pair exceeds a threshold pressure value. The processor may then pass control to the second emitter and detector pair, which may be located at a site that experiences pressures below the threshold pressure value. In an alternate embodiment (not shown), a sensor 10 may include an emitter and first detector located in a different position on the sensor body than a second detector. At step 78, a processor may note that pressure data 76 from the first emitter and first detector exceeds a threshold pressure value, and the processor may pass control to the second detector.

Figure 9:
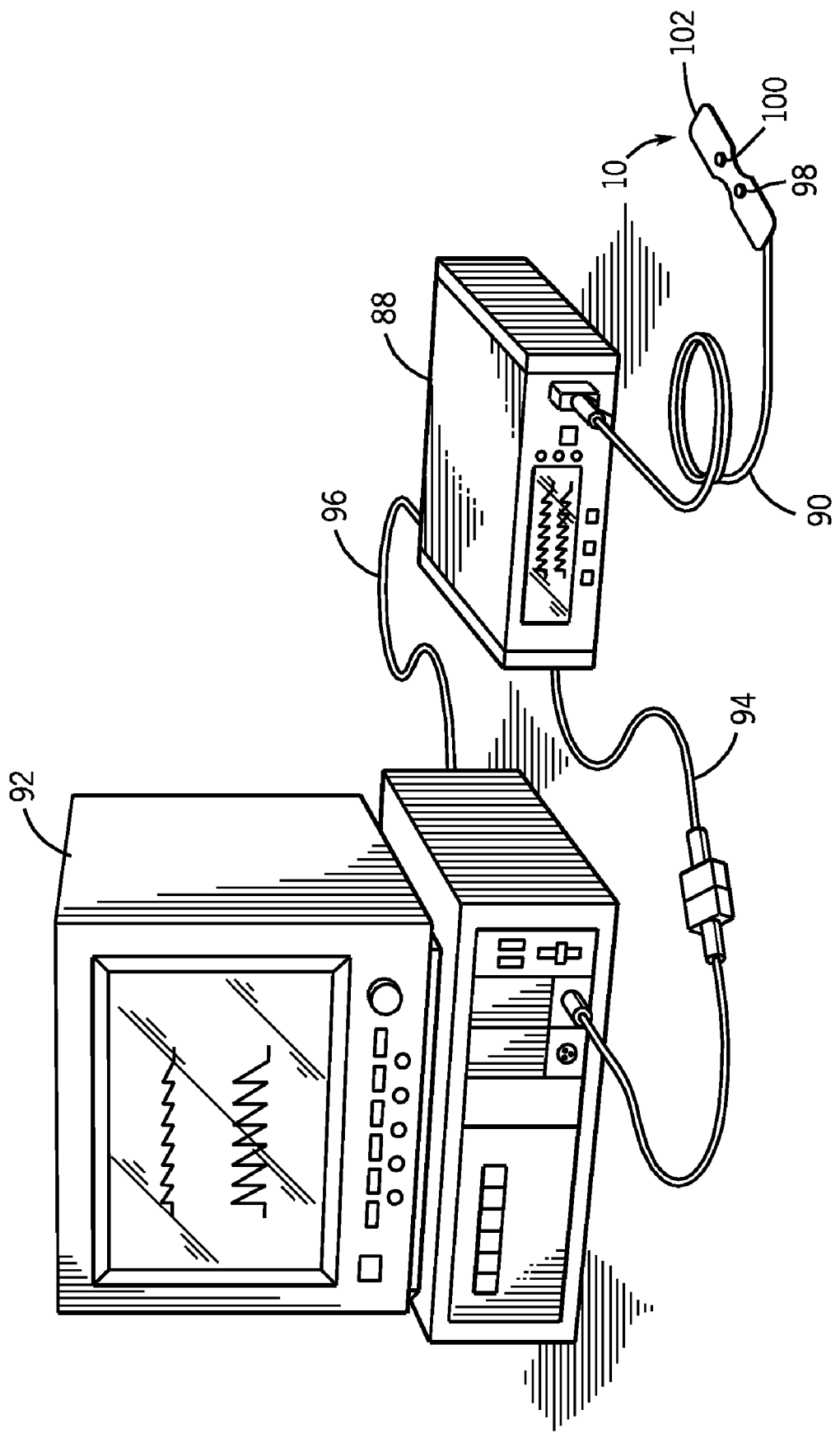
FIG. 9 illustrates a pulse oximetry system coupled to a multi-parameter patient monitor and a sensor according to embodiments of the present invention.

A sensor, illustrated generically as a sensor 10, may be used in conjunction with a pulse oximetry monitor 88, as illustrated in FIG. 9. It should be appreciated that the cable 90 of the sensor 10 may be coupled to the monitor 88 or it may be coupled to a transmission device (not shown) to facilitate wireless transmission between the sensor 10 and the monitor 88. The monitor 88 may be any suitable pulse oximeter, such as those available from Nellcor Puritan Bennett Inc. Furthermore, to upgrade conventional pulse oximetry provided by the monitor 88 to provide additional functions, the monitor 88 may be coupled to a multi-parameter patient monitor 92 via a cable 94 connected to a sensor input port or via a cable 96 connected to a digital communication port.

The sensor 10 includes an emitter 98 and a detector 100 that may be of any suitable type. For example, the emitter 98 may be one or more light emitting diodes adapted to transmit one or more wavelengths of light in the red to infrared range, and the detector 100 may one or more photodetectors selected to receive light in the range or ranges emitted from the emitter 98. Alternatively, an emitter 98 may also be a laser diode or a vertical cavity surface emitting laser (VCSEL). An emitter 98 and detector 100 may also include optical fiber sensing elements. An emitter 98 may include a broadband or "white light" source, in which case the detector could include any of a variety of elements for selecting specific wavelengths, such as reflective or refractive elements or interferometers. These kinds of emitters and/or detectors would typically be coupled to the rigid or rigidified sensor via fiber optics. Alternatively, a sensor 10 may sense light detected from the tissue is at a different wavelength from the light emitted into the tissue. Such sensors may be adapted to sense fluorescence, phosphorescence, Raman scattering, Rayleigh scattering and multi-photon events or photoacoustic effects. For pulse oximetry applications using either transmission or reflectance type sensors the oxygen saturation of the patient's arterial blood may be determined using two or more wavelengths of light, most commonly red and near infrared wavelengths. Similarly, in other applications, a tissue water fraction (or other body fluid related metric) or a concentration of one or more biochemical components in an aqueous environment may be measured using two or more wavelengths of light, most commonly near infrared wavelengths between about 1,000 nm to about 2,500 nm. It should be understood that, as used herein, the term "light" may refer to one or more of ultrasound, radio, microwave, millimeter wave, infrared, visible, ultraviolet, gamma ray or X-ray electromagnetic radiation, and may also include any wavelength within the radio, microwave, infrared, visible, ultraviolet, or X-ray spectra.

The emitter 98 and the detector 100 may be disposed on a sensor body 102, which may be made of any suitable material, such as plastic, foam, woven material, or paper. Alternatively, the emitter 98 and the detector 100 may be remotely located and optically coupled to the sensor 10 using optical fibers. In the depicted embodiments, the sensor 10 is coupled to a cable 90 that is responsible for transmitting electrical and/or optical signals to and from the emitter 98 and detector 100 of the sensor 10. The cable 90 may be permanently coupled to the sensor 10, or it may be removably coupled to the sensor 10—the latter alternative being more useful and cost efficient in situations where the sensor 10 is disposable.

The sensor 10 may be a "transmission type" sensor. Transmission type sensors include an emitter 98 and detector 100 that are typically placed on opposing sides of the sensor site. If the sensor site is a fingertip, for example, the sensor 10 is positioned over the patient's fingertip such that the emitter 98 and detector 100 lie on either side of the patient's nail bed. In other words, the sensor 10 is positioned so that the emitter 98 is located on the patient's fingernail and the detector 100 is located 180° opposite the emitter 98 on the patient's finger pad. During operation, the emitter 98 shines one or more wavelengths of light through the patient's fingertip and the light received by the detector 100 is processed to determine various physiological characteristics of the patient. In each of the embodiments discussed herein, it should be understood that the locations of the emitter 98 and the detector 100 may be exchanged. For example, the detector 100 may be located at the top of the finger and the emitter 98 may be located underneath the finger. In either arrangement, the sensor 10 will perform in substantially the same manner.

Reflectance type sensors also operate by emitting light into the tissue and detecting the light that is transmitted and scattered by the tissue. However, reflectance type sensors include an emitter 98 and detector 100 that are typically placed on the same side of the sensor site. For example, a reflectance type sensor may be placed on a patient's fingertip or forehead such that the emitter 98 and detector 100 lie side-by-side. Reflectance type sensors detect light photons that are scattered back to the detector 100. A sensor 10 may also be a "transflectance" sensor, such as a sensor that may subtend a portion of a baby's heel.

While the invention may be susceptible to various modifications and alternative forms, specific embodiments have been shown by way of example in the drawings and have been described in detail herein. However, it should be understood that the invention is not intended to be limited to the particular forms disclosed. Indeed, the present techniques may not only be applied to measurements of blood oxygen saturation, but these techniques may also be utilized for the measurement and/or analysis of other blood constituents. For example, using the same, different, or additional wavelengths, the present techniques may be utilized for the measurement and/or analysis of carboxyhemoglobin, met-hemoglobin, total hemoglobin, fractional hemoglobin, intravascular dyes, and/or water content. Rather, the invention is to cover all modifications, equivalents, and alternatives falling within the spirit and scope of the invention as defined by the following appended claims

What is claimed is:

1. A patient monitoring system comprising:
   a pulse oximetry sensor; and
   a pulse oximetry monitor coupled to the sensor, the pulse oximetry monitor being configured to:
   receive a patient signal from the pulse oximetry sensor, wherein the patient signal is related to a physiological characteristic of a patient;
   receive a pressure signal from the sensor related to a pressure between the pulse oximetry sensor and the patient;
   correlate the pressure signal to a set of reference data;
   determine a measurement of the physiological characteristic based at least in part on the patient signal;
   determine if the measurement of the physiological characteristic is associated with a signal artifact based at least in part on the pressure signal and the correlation; and
   display an indication related to the pressure signal when the signal artifact is present.

2. The system, as set forth in claim 1, wherein the indication comprises an alarm.

3. The system, as set forth in claim 2, wherein the alarm comprises at least one of a visual alarm and/or an audio alarm.

4. The system, as set forth in claim 1, wherein the signal artifact is representative of a type of patient motion.

5. The system, as set forth in claim 1, wherein the monitor is configured to correct the measurement of the physiological characteristic based at least in part on the pressure signal.

6. The system, as set forth in claim 4, wherein the patient motion comprises at least one of squeezing, scratching, tapping, and/or pressing.

7. The system, as set forth in claim 1, wherein the set of reference data comprises force data characteristic of squeezing, scratching, tapping, and/or pressing.

8. The system, as set forth in claim 1, wherein the set of reference data comprises clinical data.

9. A method comprising:
   emitting light into a tissue with an emitter;
   detecting the light with a detector;
   measuring a physiological characteristic based at least in part on the detected light;
   detecting a force experienced between the emitter or the detector and the tissue with a force-sensitive sensor;
   determining if the force indicates the presence of signal artifact; and
   correcting the measurement of the physiological characteristic when the force indicates signal artifact, wherein correcting the measurement of the physiological characteristic comprises correcting an estimated path length of the detected light between the emitter and the detector.

10. The method, as set forth in claim 9, wherein detecting a force comprises detecting a change in capacitance and/or a change in resistance.

11. The method, as set forth in claim 9, wherein detecting a force comprises detecting displacement.

12. The method, as set forth in claim 9, comprising providing an indication to a user when the force indicates signal artifact.

13. A pulse oximetry monitor comprising:
   a memory storing instructions configured to:
   acquire pressure data and oxygen saturation data from a sensor;
   correlate the acquired pressure data to a set of reference data; and
   determine if the oxygen saturation data comprises a motion artifact based at least in part on the correlation;

remove the motion artifact from the oxygen saturation data; and a processor configured to execute the instructions.

14. The pulse oximetry monitor, as set forth in claim 13, wherein correlating the acquired pressure data to the set of reference data is performed at least in part in the frequency domain.

15. The pulse oximetry monitor, as set forth in claim 14, wherein the correlating comprises a fast fourier transform or a wavelet transform.

16. The pulse oximetry monitor, as set forth in claim 13, wherein the reference data comprises data characteristic of squeezing, scratching, tapping, and/or pressing.

17. The pulse oximetry monitor, as set forth in claim 13, wherein the processor is configured to execute instructions for providing an indication to a user when the oxygen saturation data is determined to comprise the motion artifact.

18. The pulse oximetry monitor, as set forth in claim 17, wherein the indication comprises an alarm.

19. The pulse oximetry monitor, as set forth in claim 13, wherein the set of reference data comprises clinical data.

20. The pulse oximetry monitor, as set forth in claim 13, wherein the motion artifact is representative of a type of patient motion.

* * * * *